US007863043B2

(12) United States Patent
Gentry et al.

(10) Patent No.: US 7,863,043 B2
(45) Date of Patent: Jan. 4, 2011

(54) STEM CELL POPULATIONS AND METHODS OF USE

(75) Inventors: Tracy Gentry, Durham, NC (US); Sandra J. Foster, Morrisville, NC (US); Andrew E. Balber, Durham, NC (US)

(73) Assignee: Aldagen, Inc., Durham, NC (US)

( * ) Notice: Subject to any disclaimer, the term of this patent is extended or adjusted under 35 U.S.C. 154(b) by 873 days.

(21) Appl. No.: 10/589,173

(22) PCT Filed: May 4, 2004

(86) PCT No.: PCT/US2004/013747
§ 371 (c)(1),
(2), (4) Date: May 15, 2007

(87) PCT Pub. No.: WO2005/083061
PCT Pub. Date: Sep. 9, 2005

(65) Prior Publication Data
US 2008/0241171 A1 Oct. 2, 2008

Related U.S. Application Data

(60) Provisional application No. 60/543,607, filed on Feb. 11, 2004, provisional application No. 60/544,038, filed on Feb. 12, 2004.

(51) Int. Cl.
*C12N 5/08* (2006.01)
(52) U.S. Cl. ..................................................... 435/372
(58) Field of Classification Search ....................... None
See application file for complete search history.

(56) References Cited

U.S. PATENT DOCUMENTS 5,061,620 A 10/1991 Tsukamoto et al.
5,876,956 A 3/1999 Jones et al.

FOREIGN PATENT DOCUMENTS

| EP | 1 302 534 A1 | 4/2003 |
| WO | WO99/02654 | 1/1999 |
| WO | WO 00/34507 | 6/2000 |
| WO | WO 02/36751 A2 | 5/2002 |
| WO | WO 02/36751 A3 | 5/2002 |

OTHER PUBLICATIONS

Barry et al. (1999) "The Monoclonal Antibody SH-2 Raised Against Human Mesenchymal Stem Cells, Recognizes an Epitope on Endoglin (CD105)" *Biochem Biophys Res Commun* 265:134-139.
Majumdar et al. (2000) "Isolation, Characterization, and Chondrogenic Potential of Human Bone Marrow-Derived Multipotential Stromal Cells" *J Cell. Physiol.* 185:98-106.
Pittenger et al. (1999) "Multilineage Potential of Adult Human Mesenchymal Stem Cells" *Science* 284:143-147.
Cai, J., et al., "Membrane Properties of Rat Embryonic Multipotent Neural Stem Cells," *Journal of Neurochemistery*, 2004, pp. 212-226, vol. 88.
Christ, O., et al., "Short and Longterm Repopulating Cells in Human Cord Blood Display Different Levels of Aldehyde Dehydrogenase Activity as Revealed by Assays of BODIPY-Stained Cells in NOD/SCID Mice," *Blood*, 2003, vol. 102(11), Abstract No. 1178.
Fallon, P., et al., "Mobilized Peripheral Blood $SSC^{lo}$ $ALDH^{br}$ Cells Have the Phenotypic and Functional Properties of Primitive Haematopoietic Cells and Their Number Correlates With Engraftment Following Autologous Transplantation," *British Journal of Haematology*, 2003, pp. 99-108, vol. 122.
Fiordalisi, M., et al., "Surface Phenotype of Bone Marrow Cells That Express High Levels of Aldehyde Dehydrogenase (ALDH)," *Blood*, 2003, vol. 102(11), Abstract No. 4302.
Foster, S., et al., "Specificity of the Flow Cytometric Aldehyde Dehydrogenase [ALDH] Assay in Hematopoietic Progenitor Cells and Tumor Cell Lines," *Blood*, 2003, vol. 102(11), Abstract No. 3580.
Gentry, T., et al., "Aldehyde Dehydrogenase [ALDH] and Surface Antigen Expression Define Hematopoeitic Stem and Progenitor Cell [HSPC] Subsets Differentially Represented in Mobilized Peripheral Blood [PBSC], Umbilical Cord Blood [UCB], and Bone Marrow [BM]," *2004 Tandem BMT Meetings*, File name: 150245.
Hess, D., et al., "Functional Characterization of Highly Purified Human Hematopoietic Repopulating Cells Isolated Based on Aldehyde Dehydrogenase Activity," *Blood*, 2003, vol. 102(11), Abstract No. 383.
Lodie, T., et al., "Systematic Analysis of Reportedly Distinct Populations of Multipotent Bone Marrow-Derived Stem Cells Reveals a Lack of Distinction," *Tissue Engineering*, 2002, pp. 739-751, vol. 8(5).
Meyerrose, T., et al., "Isolation of Human Aldehyde Dehydrogenase—Expressing Stem Cells; A Population with Increased Homing and Hematopoietic Potential," *Blood*, 2003, vol. 102(11), Abstract No. 1175.
Storms, R., et al., "Isolation of Primitive Human Hematopoietic Progenitors on the Basis of Aldehyde Dehydrogenase Activity," *Proc. Natl. Acad. Sci. USA*, 1999, pp. 9118-9123, vol. 96.
Verfaillie, C., "Adult Stem Cells: Assessing the Case for Pluripotency," *Trends in Cell Biology*, 2002, pp. 502-508, vol. 12(11).

*Primary Examiner*—Michail A Belyavskyi
(74) *Attorney, Agent, or Firm*—Alston & Bird, LLP

(57) ABSTRACT

Populations of stem cells and methods for their isolation and use are provided. These stem cell populations comprise aldehyde dehydrogenase positive ($ALDH^{br}$) cells isolated from bone marrow, and $ALDH^{br}$ $CD105^+$ cells derived from any stem cell source. These populations may also comprise cells expressing such surface markers as CD34, CD38, CD41, CD45, CD105, CD133, CD135, CD117, and HLA-DR, and/or are substantially free from such cell surface markers as CD3, CD7, CD 10, CD 13, CD 14, C1319, CD33, CD35, CD56, CD 127, CD 138, and glycophorin A. The population may also comprise cells expressing CD90. The stem cell populations of the invention are isolated from a stem cell source such as bone marrow, peripheral blood, umbilical cord blood, and fetal liver. Methods of the invention comprise isolating and purifying stem cell populations from stem cell sources, and methods of using these cells to reconstitute, repair, and regenerate tissues.

26 Claims, 7 Drawing Sheets

Comparison of CD34 and ALDH$^{br}$ Subpopulations

Bone Marrow

| Marker | ALDH$^{br}$SSC$^{lo}$Marker$^+$ | | CD34$^+$Marker$^+$ | |
|---|---|---|---|---|
| | Mean | SD | Mean | SD |
| CD38 | 68.75 | 16.87 | 69.92 | 20.25 |
| CD45-M | 54.62 | 18.53 | 51.03 | 22.60 |
| CD105 | 10.28 | 11.17 | 1.34 | 1.26 |
| CD133 | 4.06 | 4.63 | 2.78 | 4.02 |

UCB

| Marker | ALDH$^{br}$SSC$^{lo}$Marker$^+$ | | CD34$^+$Marker$^+$ | |
|---|---|---|---|---|
| | Mean | SD | Mean | SD |
| CD38 | 49.20 | 21.90 | 47.80 | 22.84 |
| CD45-M | 78.28 | 20.45 | 75.61 | 25.07 |
| CD105 | 0.82 | 0.69 | 0.23 | 0.19 |
| CD133 | 29.61 | 21.86 | 30.74 | 24.16 |

M-PBSC

| Marker | ALDH$^{br}$SSC$^{lo}$Marker$^+$ | | CD34$^+$Marker$^+$ | |
|---|---|---|---|---|
| | Mean | SD | Mean | SD |
| CD38 | 69.17 | 26.78 | 67.65 | 27.16 |
| CD45-M | 86.08 | 21.32 | 84.27 | 23.34 |
| CD105 | 1.03 | 1.19 | 0.78 | 1.13 |
| CD133 | 36.80 | 26.15 | 35.63 | 26.73 |

Fig. 6

Hematopoeitic Progenitor Colony Assays for ALDH$^{br}$SSC$^{lo}$ Bone Marrow Cells

STEM CELL POPULATIONS AND METHODS OF USE

CROSS REFERENCE TO RELATED APPLICATION

This application is a §317 U.S. National Stage of International Application No. PCT/US2004/013747, filed May 4, 2004, which claims the benefit of U.S. Provisional Application Ser. No. 60/544,038, filed Feb. 12, 2004, and U.S. Provisional Application Ser. No. 60/543,607, filed Feb. 11, 2004, the contents of which are herein incorporated by reference in their entirety.

FIELD OF THE INVENTION

The present invention relates to populations of stem cells, methods for isolating these stem cell populations, and methods of reconstituting, repairing, and regenerating tissue using the same. The invention additionally relates to methods of screening agents that promote growth, engraftment, and differentiation of stem cells.

BACKGROUND OF THE INVENTION

Stem and progenitor cells (SPC) reproduce and maintain developmental potential until specific biological signals induce the cells to differentiate into a specific cell type or tissue type. Adult stem and progenitor cells (ASPC) are small populations of SPC that remain in tissues of an organism following birth and are continuously renewed during a lifetime. In vitro colony assays have demonstrated that bone marrow (BM), mobilized peripheral blood (MPB), and umbilical cord blood (UCB), all contain a variety of ASPC. Bone marrow is particularly rich in multipotential ASPC.

ASPC populations that give rise to a lineage are likely to be heterogeneous. Thus, not all stem cells are $CD34^+$. Similarly, while many common lymphoid progenitors are $CD7^+$ and $CD3^-$, some are $CD34^+$ and others are $CD34^-$. In part, such heterogeneity may reflect the fact that cell surface antigen expression, including CD34 expression, can depend on cell cycle or activation as well as developmental potential.

Some studies have suggested that the most primitive human hematopoietic stem cells (HSC) express the CD34 surface marker (i.e., are $CD34^+$), lack obvious lineage commitment markers (designated $Lin^-$), and express low to undetectable levels of other cell surface markers including CD38, CD71, CD45RA, and Thy-1. See, for example, Terstaypen et al. (1991) Blood 77:1218; Landsdorp et al. (1993) J. Exp. Med. 178:787; Cicuttini et al. (1994) Growth Factors 10:127; De Bruyn et al. (1995) Stem Cells 13:281; Di Giusto et al. (1994) Blood 84:421 (1994); Hao et al. (1995) Blood 86:374; Huang et al. (1994) Blood 83:1515; Muench et al. (1994) Blood 83:3170; and Rusten et al. (1994) Blood 84:1473. Conversely, other studies using long-term murine bone marrow transplant models have indicated that $CD34^{lo/-}$ cells contain a hematopoietic stem cell population that is capable of durably generating lymphoid and myeloid lineages following transplantation. See, for example, Osawa et al. (1996) Science 273:242; Morel et al. (1996) Blood 88:629a; and Jones et al. (1996) Blood 88:487, in which a population of small $Lin^-$ $CD34^{lo/-}$ $ALDH^+$ cells capable of durably generating lymphoid and myeloid lineages following engraftment was identified.

Some evidence also suggests that ASPC that appear to be committed to a certain cell lineage, such as blood cells, may retain the ability to form additional tissues, such as muscle or nerves, under appropriate conditions. For example, $CD133^+$ mesenchymal stem-like cells generally express more neuronal cell markers than $CD34^+/CD133^-$ cells (Padovan et al (2003) Cell Transplantation 12:839). Additionally, SPC become progressively restricted in their developmental potential. Thus, human stem cell populations that express CD45 and CD34, but not CD38, are highly enriched for multipotential (pluripotent) hematopoietic stem and progenitor cells; whereas, cells that express CD45, CD34, and CD38 concomitantly are more restricted developmentally. Similarly, human stem cells that generate endothelial, but not hematopoietic, colonies in vitro generally express CD31, but not CD45 or CD34. Mesenchymal stem cells generally express CD105 and CD135. Chen et al. (2002) Proc. Natl. Acad. Sci. USA. 99:15468; Chen et al. (2003) Immunity 19:525; Pierelli et al (2001) Leuk. Lymphoma. 42:1195. Morita et al. (2003) Eur. J. Haematol. 71:351.

Aldehyde dehydrogenase (ALDH) is a marker that can be used to enrich APSC. See, U.S. Pat. No. 6,537,807, herein incorporated by reference in its entirety. A fluorescent ALDH reaction product must be used to identify cells via flow cytometry because the marker is not expressed on the cell surface. See, for example, U.S. Pat. No. 6,627,759, herein incorporated by reference in its entirety. Expression of ALDH is elevated significantly in hematopoietic, neural, and potentially other types of ASPC. Cells can be further enriched by gating on low granularity, i.e., side scatter channel ($SSC^{lo}$) cells. ALDH-positive cells do not co-segregate with CD34. $CD34^+$ cell populations include $ALDH^{bright}$ ($ALDH^{br}$) and $ALDH^{dim}$ cells that, respectively, express high and low levels of enzyme (Storms et al. (1999) Proc. Natl. Acad. Sci. USA 96:9118). The $ALDH^{br}$ cells include virtually all of the stem cells, as evidenced by this cell population's ability to generate multipotential cell colonies in vitro, its ability to reconstitute NOD-SCID mice over a long term, and its ability to rapidly home to the bone marrow in NOD-SCID mice. Conversely, the $ALDH^{dim}$ populations, despite being $CD34^+$ cells, have very limited colony-forming ability, fail to home effectively, and only generate short-term reconstitution in NOD-SCID animals. Thus, ALDH expression can be used to distinguish and isolate functionally active from functionally inactive ASPC $CD34^+$ cells. Heterogeneity in umbilical cord blood (UCB) $ALDH^{br}$ populations with regard to CD45 and CD31 expression has also been reported (Hess et al. (2003) Blood, 102:383 A).

Technologies for isolating and preparing therapeutically active ASPC from bone marrow (BM) or mobilized peripheral blood (MPB) are particularly useful because the patient only needs minimally invasive procedures for stem cell therapy. Moreover, because ASPC populations are autologous, the grafts will not be subject to rejection. Allogeneic ASPC populations derived from the BM, MPB, or from umbilical cord blood (UCB) of graft donors are also useful. However, to prevent graft rejection, histocompatible donors and immunosuppressive protocols that do not interfere with graft function are needed.

The therapeutic utility of ASPC is well established, and, while not being bound by any mechanism of action or theory, considerable evidence exists that ASPC cell populations can also generate non-hematopoietic tissues in transplant recipients. See, for example, Verfaillie (2002) Trends in Cell Biol. 12:502; Ferrari et al. (1998) Science 279:1528; Gussoni et al. (1999) Nature 401:390-394; Orlic et al. (2001) Nature 410: 701-705; Jackson et al. (2001) J. Clin. Invest. 107:1395-1402; Grant et al. (2002) Nat. Med. 8:607-602; Mezey et al. (2001) Science 290:1779-1782; Brazelton et al. (2000) Science 290: 1775-1779; Krause et al. (2001) Cell 105:369-377; Petersen et al. (1999) *Science* 284:1168-1170; Lagasse et al. (2000) *Nat. Med.* 6:1229-1234; Rehman et al. (2003) *Circulation* 107:1164-1169. In addition, some evidence suggests that transplanted ASPC induce host stem cells to repair tissues (Verfaillie (2002) *Trends in Cell Biol.* 12:502). However, because cell populations from stem cell sources contain only a small percentage of ASPC, there is a need for methods of identifying the functional minority versus the non-functional majority. Once these cells are identified, therapies can be improved using custom-engineered grafts that not only contain all necessary cells for a therapeutic result, but also lack potentially dangerous, contaminating cells. Moreover, identification methods allow the useful ASPC to be concentrated, which reduces the amount of material that must be transplanted, thereby reducing tissue damage and toxicity and increasing efficacy. In addition, such selected cells can be used to generate mesenchymal cells that can be used to repair or replace tissues such as nerves, muscles, and endothelium. Stem cells can also be propagated in vitro and expanded into mesenchymal and hematopoietic cell lines to further increase the number of SPC or tissue cells that can be used for transplantation.

SUMMARY OF THE INVENTION

Populations of stem cells and methods for their isolation and use are provided. These stem cell populations comprise aldehyde dehydrogenase positive (ALDH$^{br}$) cells isolated from bone marrow, and ALDH$^{br}$ CD105$^+$ cells derived from any stem cell source. These populations may also comprise cells expressing such surface markers as CD34, CD38, CD41, CD45, CD105, CD133, CD135, CD117, and HLA-DR, and/or are substantially free from such cell surface markers as CD3, CD7, CD10, CD13, CD14, CD19, CD33, CD35, CD56, CD127, CD138, and glycophorin A. The population may also comprise cells expressing CD90. The stem cell populations of the invention are isolated from a stem cell source such as bone marrow, peripheral blood, umbilical cord blood, and fetal liver.

Methods of the invention comprise isolating and purifying stem cell populations from stem cell sources, and methods of using these cells to reconstitute, repair, and regenerate tissues.

BRIEF DESCRIPTION OF THE DRAWINGS

FIG. 6 shows a comparison of CD34$^+$ALDH$^{br}$ subpopulations from Example 1.

DETAILED DESCRIPTION OF THE INVENTION

Figure 1:
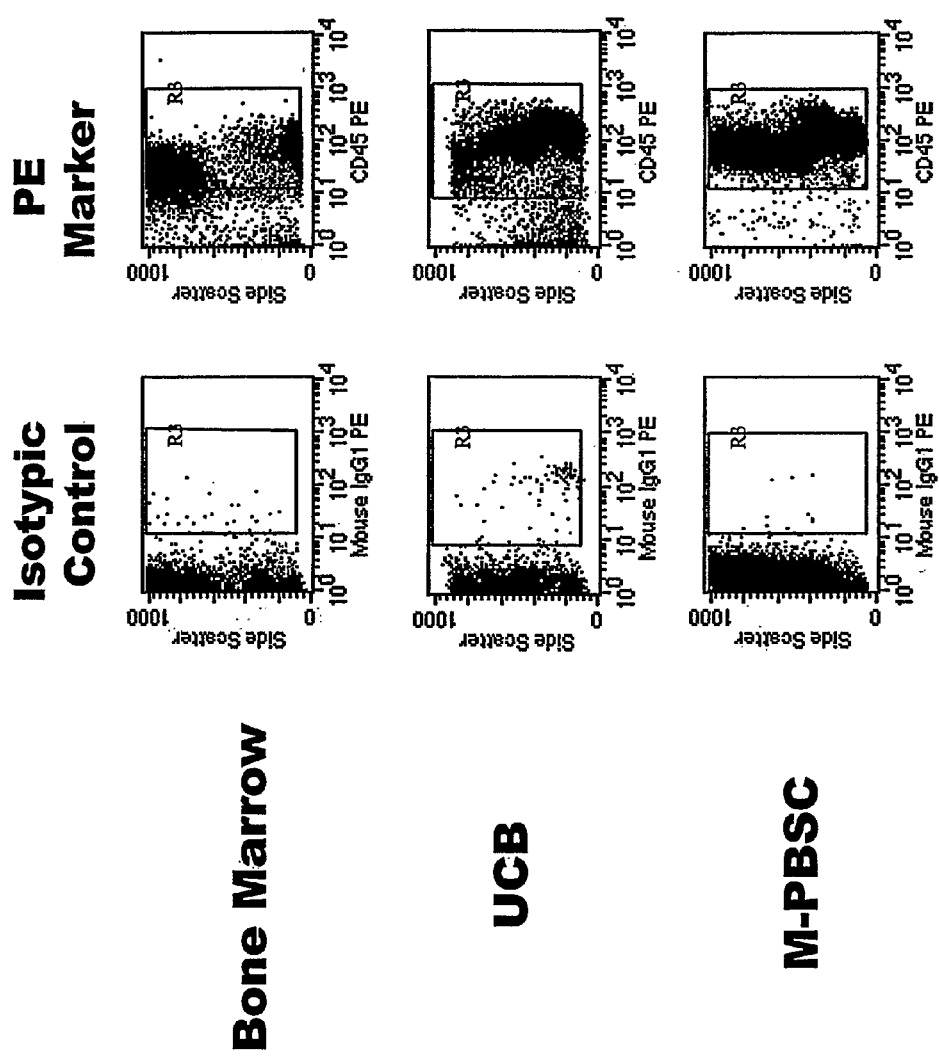
FIG. 1 shows the scatterplots from Example 1 for the isotype and fluorescent controls.
Figure 2:
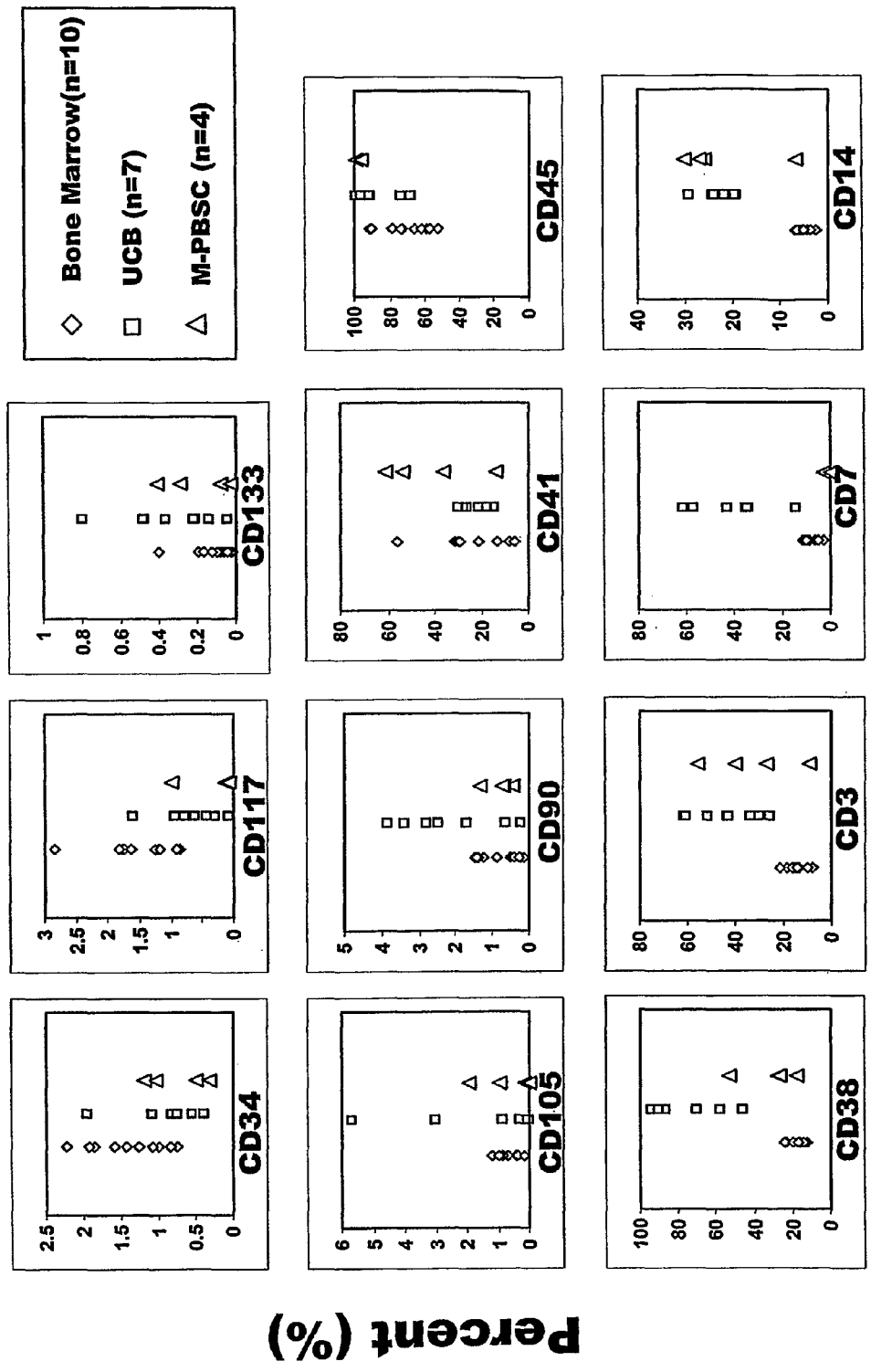
FIG. 2 shows the expression of surface markers from Example 1.
Figure 3:
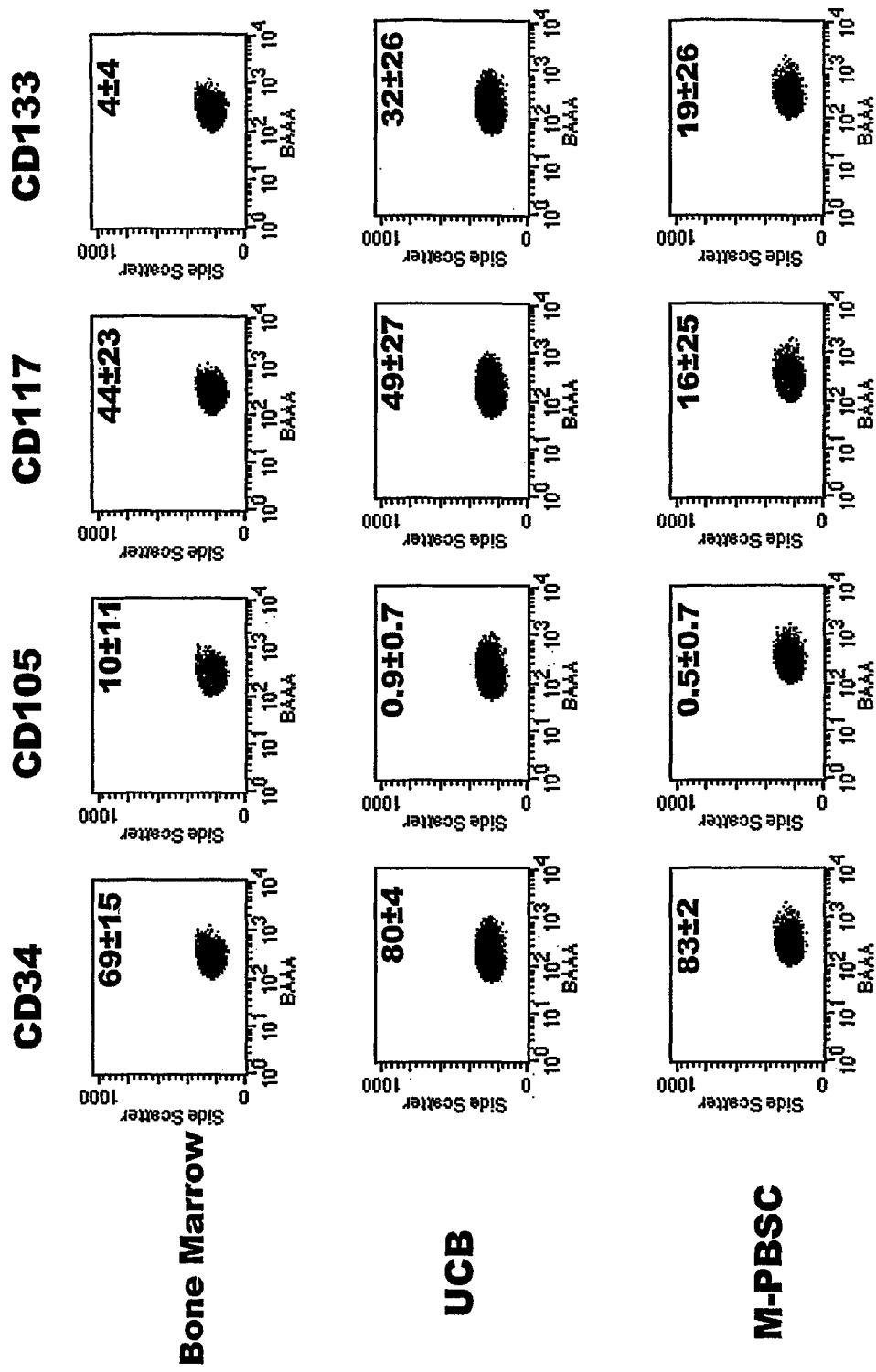
FIG. 3 shows a gated scatterplot from Example 1 of the expression of ALDH$^{br}$SSC$^{lo}$ in different grafts.
Figure 4:
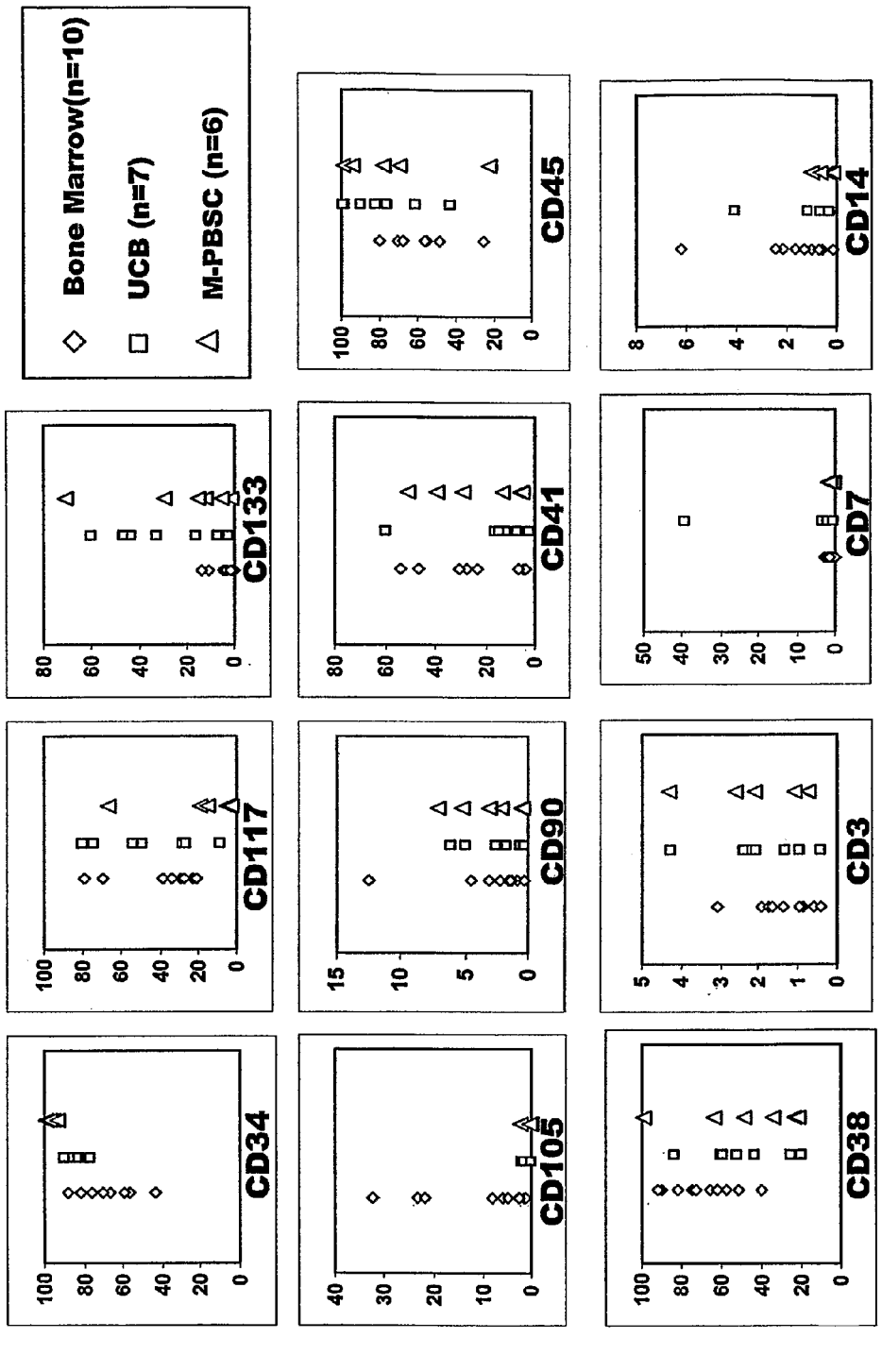
FIG. 4 shows the expression of ALDH$^{br}$SSC$^{lo}$, cell populations in different grafts for each test subject from Example 1.
Figure 5:
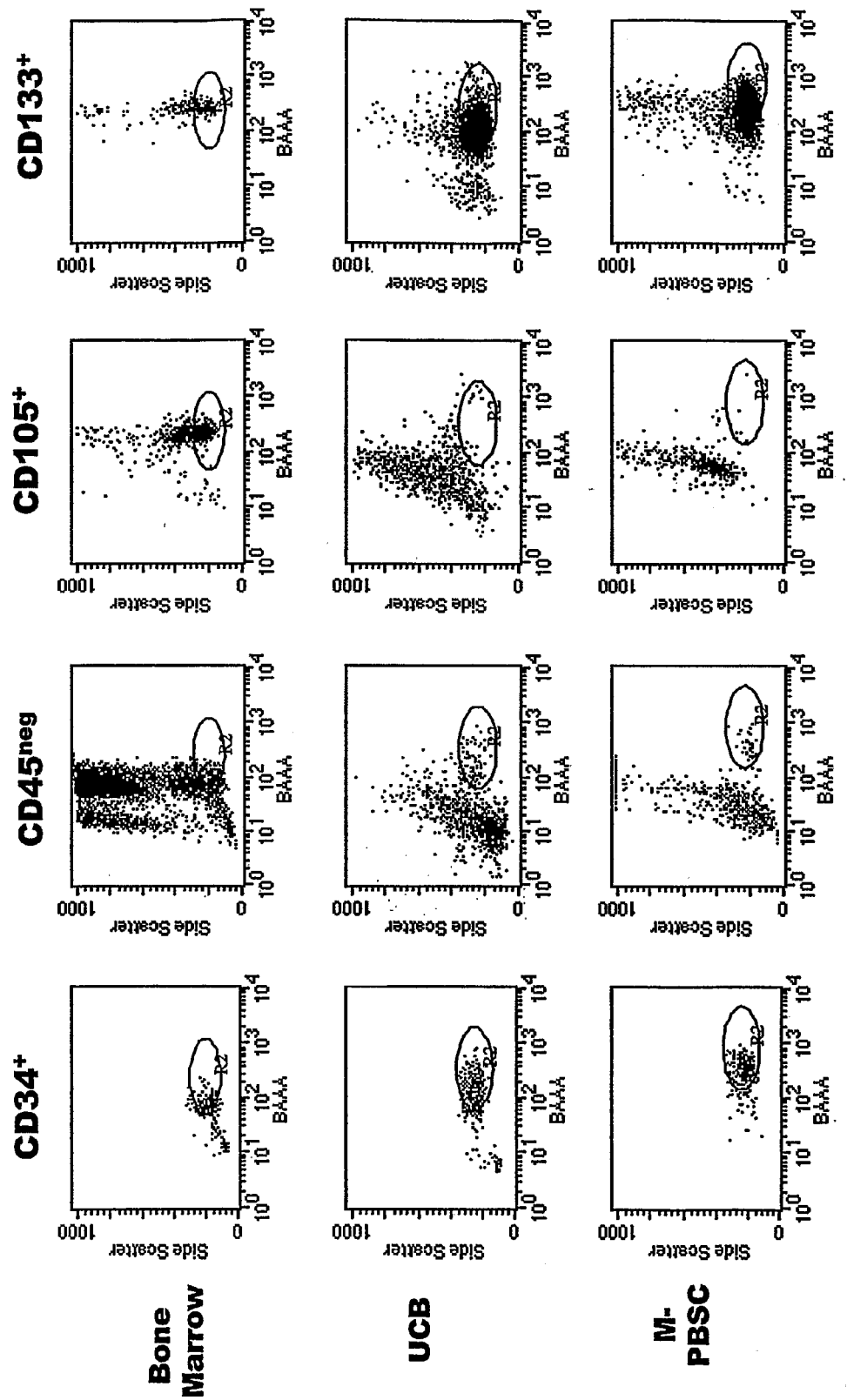
FIG. 5 shows the scatterplots from Example 1 for ALDH$^{br}$ and ALDH$_{dim}$ cells from bone marrow, umbilical cord blood, and mobilized peripheral blood are shown for cells expressing CD34, CD105, CD133, and negative for expression of CD45.

The present invention is directed to populations of stem cells, methods for isolating these stem cell populations, and methods of using these stem cell populations to reconstitute, regenerate, or repair tissue. These stem cell populations comprise stem and progenitor cells (SPC) that are ALDH$^{br}$, and, thus, contain most or all of the stem cells present in a stem cell source. The ALDH$^{br}$ cell population further comprises subpopulations of cells that express combinations of cell markers, such as CD105, or have low granularity (as measured by flow cytometry), that serve to identify those subpopulations useful for particular embodiments of the invention such as for reconstituting, regenerating, or repairing a disease of interest or for manufacturing kits.

Using a combination of cell surface markers and others markers such as intracellular enzymes and the light scattering properties of the cells, stem cell grafts of the invention can be advantageously "tailored" for particular therapeutic uses. Also, because some of these unique stem cell populations represent certain cell lineages, the populations can be used to both selectively reconstitute certain cell lineages in vivo. Stem cells that give rise to hematopoietic lineages can be used to increase the concentration and potency of stem cell grafts and, thereby, decrease toxicity. Advantageously, these cells can be sorted from autologous bone marrow and peripheral blood, thus further reducing the chance of rejection and increasing the efficacy of stem cell grafts. Stem cells that give rise to mesenchymal tissues such as bone, nerves, oligodendrocytes, muscles, vasculature, bone marrow stroma, and dermis can be used to repair or replace diseased or damaged tissues. Thus, the novel combination of CD markers disclosed herein confers such additional advantages as identification of the stem cell sources that are functionally and quantitatively best for use in isolating cells for stem cell grafts. By "isolated" is intended stem cells collected from a mammal and contacted with a cell marker, including but not limited to an antibody (conjugated or unconjugated), a fluorescent marker, an enzymatic marker, a dye, a stain, and the like.

By "cell surface marker" is intended a protein expressed on the surface of a cell, which is detectable via specific antibodies. Cell surface markers that are useful in the invention include, but are not limited to, the CD (clusters of differentiation) antigens CD1a, CD2, CD3, CD5, CD7, CD8, CD10, CD13, CD14, CD16, CD19, CD29, CD31, CD33, CD34, CD35, CD38, CD41, CD45, CD56, CD71, CD73, CD90, CD105, CD115, CD117, CD124, CD127, CD130, CD138, CD144, CD166, HLA-A, HLA-B, HLA-C, HLA-DR, VEGF receptor 1 (VEGF-R1), VEGF receptor-2 (VEGF-R2), and glycophorin A. By "intracellular marker" is intended expression of a gene or gene product such as an enzyme that is detectable. For example, aldehyde dehydrogenase (ALDH) is an intracellular enzyme that is expressed in most hematopoietic stem cells. It can be detected via flow cytometry by using fluorescent substrates.

Populations may be further analyzed based on light scattering properties of the cells based on side scatter channel (SSC) brightness and forward scatter channel (FSC) brightness. By "side scatter" is intended the amount of light scattered orthogonally (about 90° from the direction of the laser source), as measured by flow cytometry. By "forward scatter" is intended the amount of light scattered generally less than 90° from the direction of the light source. Generally, as cell granularity increases, the side scatter increases and as cell diameter increases, the forward scatter increases. Side scatter and forward scatter are measured as intensity of light. Those skilled in the art recognize that the amount of side scatter can be differentiated using user-defined settings. By the terms "low side scatter" and "SSC$^{lo}$" is intended less than about 50% intensity, less than about 40% intensity, less than about 30% intensity, or even less intensity, in the side scatter channel of the flow cytometer. Conversely, "high side scatter" or "SSC$^{hi}$" cells are the reciprocal population of cells that are not SSC$^{lo}$. Forward scatter is defined in the same manner as side scatter but the light is collected in forward scatter channel. Thus, the embodiments of the invention include selection of stem cell populations based on combinations of cell surface markers, intracellular markers, and the light scattering properties of cells obtained from a stem cell source.

The populations of stem cells disclosed herein can comprise ALDH$^{br}$ cells that can be sorted based on the positive expression of markers. By "positive for expression" is intended the marker of interest, whether intracellular or extracellular, is detectable in or on a cell using any method, including, but not limited to, flow cytometry. The terms "positive for expression," "positively expressing," "expressing," "+" used in superscript, and "$^{pos}$" used in superscript are used interchangeably herein. By "negative for expression" is intended the marker of interest, whether intracellular or extracellular, is not detectable in or on a cell using any method, including but not limited to flow cytometry. The terms "negative for expression," "negative expressing", "not expressing," "−" used in superscript, and "$^{neg}$" used in superscript are used interchangeably herein.

By "$^{br}$" used in superscript is intended positive expression of a marker of interest that is brighter as measured by fluorescence (using for example FACS) than other cells also positive for expression. Those skilled in the art recognize that brightness is based on a threshold of detection. Generally, one of skill in the art will analyze the negative control tube first, and set a gate (bitmap) around the population of interest by FSC and SSC and adjust the photomultiplier tube voltages and gains for fluorescence in the desired emission wavelengths, such that 97% of the cells appear unstained for the fluorescence marker with the negative control. Once these parameters are established, stained cells are analyzed and fluorescence recorded as relative to the unstained fluorescent cell population. As used herein the term "bright" or "$^{br}$" in superscript is intended greater than about 20-fold, greater than about 30-fold, greater than about 40-fold, greater than about 50-fold, greater than about 60-fold, greater than about 70-fold, greater than about 80-fold, greater than about 90-fold, greater than about 100-fold, or more, increase in detectable fluorescence relative to unstained control cells. Conversely, as used herein, the terms "dim" or "$^{dim}$" in superscript is intended the reciprocal population of those defined as "bright" or "$^{br}$".

In some embodiments, cells within a population of interest express markers such as CD29, the integrin β1 subunit expressed on most cells; CD31, a homotypic adhesion molecule found on all endothelial cells and some platelets and leukocytes; CD34, a highly glycosylated type I transmembrane protein expressed on 1-4% of bone marrow cells; CD38, a type II transmembrane protein found on immature T and B cells but not most mature peripheral lymphocytes; CD41, the integrin αIIb subunit that is expressed on platelets and megakaryocytes; CD45, the leukocyte common antigen found on all cells of hematopoietic origin; CD73, an ecto-5'-nucleotidase differentially expressed on subsets of mature lymphocytes and some endothelial and epithelial cells; CD90, a GPI-cell anchored molecule found on prothymocyte cells in humans; CD105, a disulfide-linked homodimer found on endothelial cells but absent from most T and B cells; CD115, the macrophage colony stimulating factor receptor expressed primarily on cells of the mononuclear-phagocytic lineage; CD117, the c-kit ligand receptor found on 1-4% of bone marrow stem cells; CD133, a pentaspan transmembrane glycoprotein expressed on primitive hematopoietic progenitor cells; CD135, the Flt3 ligand receptor that is expressed on CD34$^+$ hematopoietic stem cells; CD138, an extracellular matrix receptor expressed on immature B cells and plasma cells; CD144, the VE-cadherin molecule that organizes adheres junction in endothelial cells; CD166, found on thymic epithelium, activated T cells, and neurons; HLA-A, HLA-B, HLA-C, forms of the MHC Class I molecule; HLA-DR, the MHC Class II molecule; the VEGF receptors 1 and 2, found on hematopoietic stem cells and vascular endothelium; and any combinations of these markers.

In one embodiment, the population of cells comprises ALDH$^{br}$ cells wherein at least 10% to 100% of the cells express at least CD41, at least CD105, or at least HLA-DR. In another embodiment, the population of cells comprises ALDH$^{br}$ SSC$^{lo}$ cells wherein at least 10% to 100% of the cells express any combination of CD41, CD105, and HLA-DR.

In some embodiments, the lack of expression of a cell surface marker defines stem cell populations of the invention. Examples include populations of stem cells comprising ALDH$^{br}$ SSC$^{lo}$ cells substantially free of cells expressing the following markers: CD1a, a lymphoid marker structurally similar to MHC Class I; CD2, a pan lymphoid marker associated with antigen recognition; CD3, a member of the T cell receptor complex; CD5, expressed on mature T and B cells; CD7, an early T cell lineage marker; CD10, a type II membrane metalloprotease expressed on early T and B cell precursors; CD13, a type II membrane metalloprotease expressed on granulocytes monocytes and their precursors; CD14, a GPI-linked protein expressed mainly on myelomonocytic lineage cells; CD19, a component of the B cell antigen signaling complex; CD33, a sialic acid binding protein that is absent from pluripotent stem cells but appears on myelomonocytic precursors after CD34; CD35, the complement receptor type 1, which is expressed on many lymphoid and myelomonocytic cells; CD56, an isoform of the neural adhesion molecule found exclusively on natural killer (NK) cells; CD127, the high affinity interleukin 7 receptor expressed on lymphocytes; CD138, an extracellular matrix receptor found on immature B cells and plasma cells; glycophorin A, asialoglycoprotein present on human red blood cells and embryoid precursors; and any combinations of these markers. In some embodiments stem cells are Lin$^-$; these stem cells do not yet express lineage-commitment cell surface markers, and therefore comprise a greater number of hematopoietic stem cells. By the term "Lin$^-$" is intended that the cell lacks expression of the cell surface markers CD2, CD3, CD14, CD16, CD19, CD24, CD56, CD66b, CD14, and glycophorin A (gly A).

Based on these unique cell surface marker signatures, individual stem cell populations having unique functional characteristics have been identified.

In some embodiments at least 10%, 20%, or 30% of the ALDH$^{br}$ cells within a stem cell population of the invention express the cell markers of interest; in other embodiments at least 40%, 50%, or 60% of the ALDH$^{br}$ cells within the stem cell population express the cell markers of interest; in yet other embodiments at least 70%, 80%, or 90% of the ALDH$^{br}$ cells within the stem cell population express the cell markers of interest; in still other embodiments at least 95%, 96%, 97%, 98%, 99%, or even 100% of the ALDH$^{br}$ cells within the stem cell population express the cell markers of interest. By "substantially free" is intended less than about 5%, 4%, 3%, 2%, 1%, or even 0% of the cells in the population express the marker of interest. While the isolation of purified cell population from bone marrow is specifically exemplified herein, the isolation of such cells from other sources, including umbilical cord blood, peripheral blood, and fetal liver, is also contemplated.

Selective methods known in the art and described herein can be used to further characterize SPC, including ASPC. Commonly, sources of SPC and ASPC are reacted with monoclonal antibodies, and subpopulations of cells expressing cognate cell surface antigens are either positively or negatively selected with immunomagnetic beads by complement mediated lysis, agglutination methods, or fluorescence activated cell sorting (FACS). The functional attributes of the resulting subpopulations with a defined cell surface phenotype are then determined using a colony-forming assay. Once the phenotype of cells that do and do not have SPC or ASPC activity is known, these methods can be used to select appropriate SPC or ASPC for therapeutic transplantation.

If desired, a large proportion of terminally differentiated cells may be removed by initially using a negative selection separation step. For example, magnetic bead separations may be used initially to remove large numbers of lineage committed cells. Desirably, at least about 80%, usually at least about 70% of the total cells, will be removed.

Procedures for cell separation may include, but are not limited to, positive or negative selection by means of magnetic separation using antibody-coated magnetic beads, affinity chromatography, cytotoxic agents joined to a monoclonal antibody or used in conjunction with a monoclonal antibody, including, but not limited to, complement and cytotoxins, and "panning" with antibody attached to a solid matrix, e.g., plate, elutriation, or any other convenient technique.

Techniques providing accurate cell separation include, but are not limited to, flow cytometry, which can have varying degrees of sophistication, e.g., a plurality of color channels, low angle and obtuse light scattering detecting channels, impedance channels, and the like. The antibodies for the various dedicated lineages may be illuminated by different fluorochromes. Fluorochromes that may find use in a multicolor analysis include phycobiliproteins, e.g., phycoerythrin and allophycocyanins; fluorescein; and Texas red. The cells may also be selected against dead cells, by employing dyes that selectively accumulate in dead cells (e.g., propidium iodide and 7-aminoactinomycin D (7-AAD)). Preferably, the cells are collected in a medium comprising about 2% fetal calf serum (FCS) or 0.2% bovine serum albumin (BSA). See, for example, Fallon et al. (2003) *Br. J. Haematol.* 121:1, herein incorporated by reference.

Other techniques for positive selection may be employed, which permit accurate separation, such as affinity columns, and the like. The method of choice should permit the removal of the non-progenitor cells to a residual amount of less than about 20%, less than about 15%, less than about 10%, or less than about 5% of the desired population of stem cells.

The stem cell populations of the invention can be isolated from stem cell sources using a variety of methods, including those described herein and exemplified below. For example, in one embodiment, a two-step procedure can be used. For example in a first step, stem cells are positively selected by first sorting for cellular expression of ALDH$^{br}$, for example by using FACS. In a second step, cells are either positively selected by sorted for expression of cell surface markers such as CD105, HLA-DR, CD41, or negatively sorting for lack of expression of cell surface markers such as lineage commitment markers.

Alternatively, a three-step isolation procedure can be used. In a first step, mature mononuclear cells, for example, which express any of the different surface antigens associated with specific lineage commitment, can be eliminated using a commercially available kit from StemCell Technologies. The resulting preparation, designated Lin$^-$, is essentially devoid of cells expressing any of the following surface antigens: glycophorin A (glyA), CD2, CD3, CD14, CD16, CD19, CD24, CD56, and CD66b. In a second step, a subset of Lin$^-$ cells can be sorted by flow cytometry after staining with, for example, BODIPY aminoacetaldehyde, to obtain ALDH$^{br}$ Lin$^-$ and ALDH$^{lo}$Lin$^-$. In a third step, CD34$^+$ cells can be sorted from the ALDH$^{br}$ Lin$^-$ fraction using, for example, flow cytometry, to yield ALDH$^{br}$ CD34$^-$ Lin$^-$ cells and ALDH$^{br}$ CD34$^+$Lin$^-$ cells. This preparation can further be sorted for cells positively expressing CD13, CD33, CD35, CD38, CD41, CD45, CD90, CD105, CD117, CD133, CD135, CD138, HLA-DR, or any combinations thereof.

In an alternative embodiment, the isolation procedure involves the use of a single negative depletion step. In accordance with this procedure, cells expressing Lin lineage markers are eliminated in a single step using appropriate antibodies.

Regardless of the isolation procedure used, the resulting cells have properties of multilineage stem cells. By "multilineage stem cells" is intended cells capable of multilineage development into cells such as mesenchymal stem cells (MSC), hematopoietic stem cells (HSC), or self-renewing progenitor cells that are themselves capable of MSC or HSC development. By "multilineage development" is intended capable of developing into any differentiated tissue including, but not limited to, blood cells (including lymphocytes, myelocytes, erythrocytes, and platelets); bone (including osteocytes, osteoblasts, and osteoclasts); marrow stroma; cartilage (including chrondrocytes, chrondroblasts, and chrondroclasts); cardiac, smooth, and skeletal muscle (including myocytes and cardiomyocytes); tendon; nerves (including oligodendrocytes and neurons); vascular tissue (including angiocytes and the endothelium); fat (including adipocytes); fibroblasts; liver cells; gut and lung epithelial cells; cornea (including corneocytes; and dermis (including dermal cells). By "hematopoietic stem cells" is intended stem cells that differentiate into blood cells. By "mesenchymal stem cells" is intended stem cells that differentiate into non-blood cells. SPC and ASPC comprise multilineage stem cells capable of developing into either mesenchymal stem cells or hematopoietic stem cells.

Hematopoietic stem cells do not express cell surface markers for immature and mature lymphocytes, erythrocytes, or myeloid cells, unlike lineage-committed precursors. More specifically, they have no detectable expression of surface markers of myeloid cells (CD33), B-lymphocytes (CD19, HLA-DR), T-lymphocytes (CD3, CD4, CD8), NK cells (CD16, CD56), or erythroid cells (CD71), where expression is detected using fluorescence-conjugated antibodies. Hematopoietic stem cells also do not have detectable expression of the early lymphoid markers CD1a, CD2, CD5, or CD10, which are present on committed lymphoid precursors. Advantageously, the primitive hematopoietic stem cells of the invention do not have detectable expression of any of the following antigens: CD3, CD4, CD8, CD13, CD14, CD16, CD19, CD25, CD33, CD56, CD71, CD124, CD130, CD138, or glyA. Preferably, the ALDH$^{br}$ stem cells are also capable of sustaining long-term hematopoiesis in mice (see, for example, Goodell et al. (1996) *J. Exp. Med.* 183:1797). More preferably, they are in $G_0$, a cell cycle state that is believed to be a property of primitive hematopoietic cells (Spangrade et al. (1990) *Proc. Natl. Acad. Sci. USA* 87:7433).

In one embodiment, the stem cells of the invention comprise $ALDH^{br}$ cells derived from bone marrow. These $ALDH^{br}$ cells can be used to generate any cell of the hematopoietic lineage, including, but not limited to, myeloid cells (such as platelets, megakaryocytes, and red bloods cells) and lymphoid cells (such as T cells, B cells, NK cells, and antigen presenting cells). In an alternative embodiment, the stem cell of the invention can comprise $ALDH^{br}$ $CD105^+$ cells isolated from any stem cell source, not just bone marrow. These cells are also capable of generating any cell of the hematopoietic lineage, including, but not limited to, myeloid cells (such as platelets, megakaryocytes, and red bloods cells) and lymphoid cells (such as T cells, B cells, NK cells, and antigen presenting cells). In an alternative embodiment, the $ALDH^{br}$ cells derived from bone marrow or the $ALDH^{br}CD 105^+$ cells isolated from any stem cell source comprise cells with a low granularity as measured in the side scatter channel of a flow cytometer ($SSC^{lo}$).

Mesenchymal stem cells (MSC) have been characterized using panels of antibodies much like hematopoietic stem cells. MSC generally lack expression of CD14, CD34, and CD45. MSC are generally positive for CD105 and CD73. Other markers used by researchers to identify cultured mesenchymal cells include positive expression of such markers as CD29, Thy-1 (CD90), CD115, CD144, CD166, and HLA-A, B, or C. Functionally, MSC can be tested in vitro for their ability to differentiate into adipogenic, osteogenic, myogenic, and chondrogenic cell colonies.

As disclosed supra, the stem cells of the invention comprise $ALDH^{br}$ cells derived from bone marrow. These $ALDH^{br}$ cells can be also used to at least generate any cell of the mesenchymal lineage, including, but not limited to, bone (including osteocytes, osteoblasts, and osteoclasts), marrow stroma, cartilage (including chrondrocytes, chrondroblasts, and chrondroclasts), cardiac, smooth, and skeletal muscle (including myocytes and cardiomyocytes), tendon, nerves (including oligodendrocytes and neurons), vascular tissue (including the endothelium), fat (including adipocytes), fibroblasts, and dermis. In an alternative embodiment, the stem cell of the invention can comprise $ALDH^{br}$ $CD105^+$ cells isolated from any stem cell source, not just bone marrow. These cells are also capable of generating any cell of the mesenchymal lineage, including, but not limited to, bone (including osteocytes, osteoblasts and osteoclasts), marrow stroma, cartilage (including chrondrocytes, chrondroblasts, and chrondroclasts), cardiac, smooth, and skeletal muscle (including myocytes and cardiomyocytes), tendon, nerves (including oligodendrocytes and neurons), vascular tissue (including the endothelium), fat (including adipocytes), fibroblasts, and dermis. In an alternative embodiment the $ALDH^{br}$ cells derived from bone marrow or the ALDH r $CD105^+$ cells isolated from any stem cell source comprise cells with a low granularity as measured in the side scatter channel of a flow cytometer ($SSC^{lo}$).

In some embodiments, the stem cell populations of the invention isolated from bone marrow, for example, are $ALDH_{dim}$ and comprise cells that are CD45 negative. In other embodiments, the stem cell populations of the invention isolated from bone marrow, for example, are $ALDH^{br}$ and comprise cells that are CD45 negative. In yet other embodiments, the stem cell population isolated from umbilical cord blood and mobilized peripheral blood, for example, are $ALDH^{br}$ and are CD45 negative. In yet other embodiments, the stem cell population isolated from umbilical cord blood and mobilized peripheral blood, for example, are $ALDH^{dim}$ and are CD45 negative.

Functional assays for stem cells include both in vitro and in vivo methods. For in vitro tests, cultures are seeded with cells from tissues under conditions that favor the differentiation of SPC or ASPC into specific types of tissue cells. See, for example, Eaves, "Assays of Hematopoictic Progenitor Cells" in Williams (1995) *Hematology* at L22-6 ($5^{th}$ ed., E. Beutler et al. eds.); Petzer et al. (1996) *Proc. Natl. Acad. Sci. USA* 93:1470; Mayani et al. (1993) *Blood* 81:3252; Hogge et al. (1997) *Br. J. Haematol.* 96:790; Lazarus et al. (1995) *Bone Marrow Transplant.* 16:557; Pittenger et al. (1999) *Science* 284:143.

Usually, ASPC will multiply a few times in culture as they differentiate to form a colony of differentiated cells. In some assays, such as assays involving blood cell differentiation, the developmental potential of a cell that initiated the colony is inferred from the range of phenotypes within the colony. Alternatively, cell cultures may be sampled and subcultured into a different culture system or into animal models, such as immunodeficient NOD-SCID mice or sheep embryos, to determine if additional phenotypes can be induced from APSC that remain in the individual colony. See, for example, Almeida-Porada et al. (2000) *Blood* 95:3620; Lewis et al. (2001) *Blood* 97:3441; Rice et al. (2000) *Transplantation* 69:927; Ishikawa et al. (2002) *Exp. Hematol* 30:488. ASPC that give rise to multiple phenotypes are usually considered more primitive, multipotent progenitors than cells that give rise to fewer phenotypes.

Based on these assays, the choice of a starting stem cell source coupled with the specific lineage-preferred cell population allows for a variety of therapeutic applications using one or a few ASPC types. For example, $ALDH^{br}$ cell populations that have been isolated by sorting BM include more mesenchymal stem cells capable of giving rise to non-hematopoietic tissues than do $ALDH^{br}$ cell populations derived from MPB or UCB based on the increased percentage of cells expressing early mesenchymal stem cell markers such as CD105. See, Example 1, Table 1, herein below.

The stem cell populations of the present invention have application in a variety of therapies and diagnostic regimens. They are preferably diluted in a suitable carrier such as buffered saline before injection. The cells may be administered in any physiologically acceptable vehicle, normally intravascularly, although they may also be introduced into bone or other convenient site where the cells may find an appropriate site for regeneration and differentiation (e.g., thymus). Usually, at least $1 \times 10^5$ cells/kg and preferably $1 \times 10^6$ cells/kg or more will be administered. See, for example, Sezer et al. (2000) *J. Clin. Oncol.* 18:3319 and Siena et al. (2000) *J. Clin. Oncol.* 18:1360. The cells may be introduced by injection, catheter, or the like. If desired, additional drugs such as 5-fluorouracil and/or growth factors may also be co-introduced. Suitable growth factors include, but are not limited to, cytokines such as IL-2, IL-3, IL-6, IL-11, G-CSF, M-CSF, GM-CSF, gamma-interferon, and erythropoietin. In some embodiments, the cell populations of the invention can be administered in combination with other cell populations that support or enhance engraftment, by any means including but not limited to secretion of beneficial cytokines and/or presentation of cell surface proteins that are capable of delivering signals that induce stem cell growth, homing, or differentiation. In these embodiments, less than 100% of the graft population comprise the $ALDH^{br}$ stem cells.

As the isolated cells of the invention are capable of engrafting hematopoietic stem cells, they are suitable for both transplantation and gene therapy purposes. Since the populations of cells can be sorted into both lineage-committed and lineage-uncommitted cells, each population will have different, but non-mutually exclusive, therapeutic applications. In some embodiments, lineage-committed cells will be useful for reconstitution or augmentation of lymphoid and/or myeloid cell populations. For example, indications to be treated include immunodeficiency's and stem cell transplantations. The progenitor cells are particularly useful during stem cell transplantation to decrease the lag time between the transplantation and repopulation of the hematopoietic cells. Methods of obtaining the progenitor cells are described herein. Methods of administering stem cells to patients are within the skill of one in the art as noted herein above.

In some embodiments, identification of a lymphoid-restricted progenitor cell population allows assessment of this population as to the origin of disease, e.g., leukemia, and therefore is useful in purging such cells from an autologous graft. In other embodiments, lineage-committed precursor cells may be useful as a cellular graft to increase the patient's ability to mount an immune response. In some instances, it may be advantageous to use precursors in a vaccine strategy whereby the cells are loaded with antigen and injected to induce a specific immune response. Alternatively, the injected cells may be used to induce tolerance to a specific exogenously introduced antigen.

Lineage-committed precursors may be used for a variety of gene therapy approaches where expression of the exogenous genetic capability is desired in lymphoid and/or myeloid lineages. Lineage-committed progenitor cells will also be preferred in cases where it is desired to have temporary rather than permanent expression of the exogenous genetic capability. Also, in some instances, gene transfer is likely to be more efficient in lineage-committed progenitors because progenitor cells cycle more actively than stem cells and retroviral vectors are known to require actively cycling cells for efficient integration of the recombinant DNA.

In addition, it would be advantageous to use lymphoid progenitors compared to using mature lymphoid cells for gene therapy. Currently, T cell gene therapy requires ex vivo expansion of T cells with cytokines. Upon reinfusion, the modified T cells often do not home properly to their target organs and may become trapped in (and cleared by) the lungs, liver, or spleen. This improper homing may be due to alteration of the membranes during the ex vivo processing, down-regulation of homing receptors, or the like. Use of modified progenitor cells would obviate the necessity of ex vivo expansion of the effector T cells, and thus obviate concerns of altered trafficking and persistence in vivo. In addition, the use of modified progenitors will allow amplification in progeny cell numbers, thereby reducing the need for ex vivo expansion and reducing the frequency of administration.

In other embodiments, it is preferable to use non-lineage-committed cells or more primitive stem cells. Non-lineage committed cells are useful for treating diseases (and related therapeutic sequelae) caused by the impaired function of bone marrow cells. Examples of such diseases include, but are not limited to, lymphoma, multiple myeloma, breast cancer, testicular cancer, leukemias, congenial hemolytic anemias (e.g., thalassemia), and some immunodeficiency diseases, e.g., acute leukemia, Hodgkin's and non-Hodgkin's lymphoma, and neuroblastoma. It has also been shown that the hematologic toxicity sequelae observed with multiple cycles of high-dose chemotherapy is relieved by conjunctive administration of autologous hematopoietic stem cells. Diseases for which reinfusion of stem cells has been described include acute leukemia, Hodgkin's and non-Hodgkin's lymphoma, neuroblastoma, testicular cancer, breast cancer, multiple myeloma, thalassemia, and sickle cell anemia (Cheson et al. (1989) *Ann. Intern. Med.* 30 110:51; Wheeler et al. (1990) *J. Clin. Oncol.* 8:648; Takvorian et al. (1987) *N. Engl. J. Med.* 316:1499; Yeager, et al. (1986) *N. Eng. J. Med.* 315: 141; Biron et al. (1985) In *Autologous Bone Marrow Transplantation Proceedings of the First International Symposium*, Dicke et al., eds., p. 203; Peters (1985) ABMT, id. at p. 189; Barlogie, (1993) *Leukemia* 7:1095; Sullivan, (1993) *Leukemia* 7:1098-1099).

For example, in cancer patients, sorting stem cells of the invention such as ALDH$^{br}$ bone marrow derived cells or ALDH$^{br}$ CD105$^+$ cells from any source separates stem cells from cancer cells prior to reintroduction into the patient. In these patients undergoing autologous transplantation, such separation can be used to reduce the chance that cancer cells are returned to the patient (Jones et al. (1987) Blood 70:1490; Colvin In: *Hematopoietic Cell Transplantation* 217 (Forman ed., 1999), and Russo and Hilton (1989) *in Enyzmology and Molecular Biology of Carbonyl Metabolism* at 65 (Weiner and Flynn, eds.). In another embodiment, purified autologous ALDH$^{br}$ stem cells of the invention can be ex vivo expanded prior to reintroduction into the patient to hasten lymphoid, erythroid, and platelet engraftment. Ex vivo expansion can be effected by growth in defined cytokines, on stromal layers, and/or in bioreactors (Emerson et al. (1996) *Blood* 87:3082). In addition, the incidence of graft failure can be reduced. This is beneficial for cancer patients undergoing autologous transplantation, for gene therapy, and for patients suffering from auto-immune disorders.

In some embodiments, while not being bound to any mechanism of action or theory, the population of non-lineage committed stem cells of the invention may be used to hasten healing of injuries, repair injuries, and regenerate tissues. As the cell populations of the invention can differentiate into mesenchymal tissue, the stem cells of the invention can be used beneficially in a wide variety of diseases not associated with hematopoiesis, for example joint regeneration for arthritis; bone regeneration for osteoporosis, osteoimperfecta, and periodontitis; angiogenesis and endothelial cell regeneration for ischemic injury; muscle re-growth for degenerative muscle disease such as muscular dystrophy and cardiac ischemia; neural cell regrowth in spinal cord and brain injury; regeneration of oligodendrocytes in multiple sclerosis; as well as surgeries where tissue regrowth is beneficial such as plastic surgery, orthopedic surgery, and surgical tissue removal. Thus, the mesenchymal stem cells of the invention can used to produce, in some embodiments, new endothelium, new cardiomyocytes, new neurons and oligodendrocytes, and new bone and cartilage. For example, it has been shown that mesenchymal stem cells grow endothelium, and that mesenchymal grafts treat restenosis and ischemic heart injury. See, for example, Hristov et al. (2003) *Trends Cardiovasc Med.* 13:201; Sata (2003) *Trends in Cardiovasc. Med.* 13:249; Isner et al. (2001) *Ann. NY Acad. Sci.* 953:75; Abbott and Giordano (2003) *J. Nucl. Cardiol.* 10:403; Forrester et al. (2003) *Circulation* 108:1139. It has also been shown that mesenchymal stem cell grafts promote regrowth of damaged neurons after neurological damage or disease. See, for example, Gage (2000) *Science* 287:1433; Shin et al. (2001) *Blood* 98:2412; Zhao et al. (2003) *Brain Res. Protocols* 11:38. It has also been shown that mesenchymal stem cell grafts promote new bone and cartilage growth. See, for example, Pittenger et al. (1999) *Science* 284:143, and U.S. Pat. No. 6,541,024.

In some embodiments, the isolated stem cell populations of the invention are suitable for use in gene therapy. For example, following isolation of autologous ALDH$^{br}$ cells from bone marrow or ALDH$^{br}$CD105$^+$ from any stem cell source, the isolated cells are exposed to a gene delivery vector, and the genetically modified stem cells are reinfused into the patient. Gene therapy protocols using genetically modified stem cells are known in the art. See, for example, Smith (1992) *Hematother.* 1:155. This approach can involve ex vivo culture or the use of vectors capable of transferring genes into non-dividing cells, thereby rendering ex vivo culture unnecessary. By the term "ex vivo gene therapy" is meant the in vitro transfection or retroviral infection of stem cells prior to introducing the transfected stem cells into a mammal. Gene therapy can be useful in treating, for example, congenital diseases, which include, but are not limited to, adenosine deaminase deficiency, recombinase deficiency, recombinase regulatory gene deficiency, and sickle cell anemia. In treating sickle cell anemia, for example, the mutant β-globin gene is replaced or supplemented with either the wild-type globin gene or an anti-sickling globin gene. In the treatment of cancer, drug resistance genes can be introduced into cells to confer resistance to cytotoxic drugs. This can reduce the incidence and severity of myelosuppression. For the treatment of infectious diseases, including HIV, anti-viral genes can be introduced into stem cell populations of the invention so that they are rendered resistant to the virus (see, for example, Gilboa and Smith (1994) *Trends in Genetics* 10:139).

In some embodiments, isolation of ALDH$^{br}$ cells from bone marrow or ALDH$^{br}$CD 105$^+$ from any stem cell source results in the elimination of pre-T-cells that cause graft versus host disease (GvHD). This elimination from the stem cell population of the invention can be expected to reduce the incidence and severity of GvHD in recipients of allogeneic transplants. See, for example, Ho and Soiffer (2001) *Blood* 98:3192.

Isolated ASPC can be ex vivo expanded to hasten neutrophil, erythroid, and platelet engraftment after allogeneic transplantation. In addition, the incidence of graft failure can be reduced. This is likely to be particularly important for recipients of umbilical cord blood transplants, where small cell doses limit the success of transplantation. Techniques for ex vivo expansion are well described in the art. See, for example, McNiece and Briddle (2001) *Exp. Hematol.* 29:3; McNiece et al. (2000) *Exp. Hematol.* 28:1186; Jaroscak et al. (2003) *Blood* 101:5061.

In some embodiments, successful engraftment with ALDH$^{br}$ cells from bone marrow or ALDH$^{br}$CD105$^+$ from any stem cell source can also be expected to induce tolerance to alloantigens. Prior induction of tolerance enhances the chance of permanent engraftment of subsequent solid organ transplants that originate from the same donor.

It will be appreciated that the stem cell populations of the present invention can be used as sources of new genes (e.g., for cytokines and cytokine receptors), including genes important in growth and development.

In addition to their application in treatment and diagnosis strategies, the stem cell populations of the present invention can be used in screening protocols to identify agents that can be used, for example, to promote differentiation or growth and/or engraftment of stem cells. In one such protocol, ALDH$^{br}$ cells from bone marrow or ALDH$^{br}$CD105$^+$ from any stem cell source are contacted with a test compound suspected of inducing differentiation, and the ability of the test compound to effect differentiation is determined (using, for example, microscopic and flow cytometric examination). In another screening protocol, ALDH$_{br}$ cells from bone marrow or ALDH$^{br}$CD105$^+$ from any stem cell source are contacted with a test compound suspected of inducing proliferation and/or engraftment and the ability of the test compound to effect proliferation and/or engraftment is determined, for example, using in vitro long-term colony assays or in vivo immunodeficient mice models (e.g., SCID/NOD mice). See, for example, Peault et al. (1993) *Leukemia* 7:s98-101.

The invention also relates to kits that can be used to prepare the stem cell populations of the present invention, where, in some embodiments, the populations comprise ALDH$^{br}$ cells from bone marrow or ALDH$^{br}$CD105$^+$ from any stem cell source. The kits can comprise an ALDH substrate disposed in a single container and antibodies that can be used to effect direct isolation of the cells in separate containers. In a preferred embodiment, the kit includes at least antibodies specific for lineage-specific markers disposed within one or more container means. These antibodies can be used in conjunction with those present in the StemCell Technologies kit to achieve, for example, about 80% purification or higher. Advantageously, the kit also includes antibodies specific for HLA-DR. Any or all of antibodies specific for CD2, CD3, CD8, CD10, CD13, CD14, CD16, CD19, CD33, CD34, CD35, CD38, CD41, CD45, CD56, CD71, CD105, CD117, CD124, CD127, CD130, CD138, and glyA can also be included, disposed within at least one container means. The kit can also include, disposed within a container means, anti-CD7 antibodies.

The antibodies of the kits are disposed within a container means and the kit can further include ancillary reagents (e.g., buffers and the like) suitable for carrying out the isolation protocols.

The following examples are offered by way of illustration and not by way of limitation.

EXPERIMENTAL

Example 1

Tissue Processing and Phenotyping

Directly conjugated fluorescent antibodies were employed for analyses of cell surface antigens. Those used included antibodies directed against CD3 (Leu4; Becton Dickinson clone SK7); CD7 (Leu9; Becton Dickinson clone M-T701); CD10 (Beckman Coulter/Immunotech clone ALB1); CD13 (Beckman Coulter/Immunotech clone SJ1D1); CD14 (Beckman Coulter/Immunotech clone RM052); CD19 (Leu12; Pharmingen clone WM15); CD33 (LeuM9; Becton Dickinson clone M-ϕP9); CD34 (Becton Dickinson clone 8G12); CD35 (Pharmingen clone E11); CD38 (Leu17; Becton Dickinson clone HB7); CD41 (Caltag clone VIPL3); CD45 (Miltenyi clone 5B1); CD56 (Leu19; Becton Dickinson clone My31); CD90 (Pharmingen; clone 5E10); CD105 (Caltag clone SN6); CD117 (Becton Dickinson clone 104D2); CD127 (Beckman Coulter/Immunotech clone R34.34); CD133 (Miltenyi clone AC 133); CD135 (Pharmingen clone 4G8); CD 138 (IQ products clone B-B4); HLA-DR (Becton Dickinson clone L243); and glyA (Becton Dickinson clone GAR-2).

Fresh bone marrow samples from ten normal donors (Cambrex) were diluted in ammonium chloride 1:40 by volume (0.17 M NH$_4$Cl containing 10 mM Tris-HCl, pH 7.2 and 200 mM EDTA final concentration) and incubated at 4° C. for 30 minutes to lyse erythrocytes. Cells were pelleted by centrifugation, resuspended at 1×10$^7$/ml, and reacted for aldehyde dehydrogenase activity using the ALDEFLUOR™ kit (StemCo Biomedical, Inc.). Cells were suspended in assay buffer, and 50 ml of substrate/ml were added to the cells and mixed immediately. 100 ml of cells were removed from the substrate tube and added to the diethylaminobenzaldehyde (DEAB) control tube. Cells were incubated at 37° C. for 30 minutes. 3-4×10$^6$ cells were placed in each immunophenotype tube and incubated for an additional 15 minutes at 4° C. with the appropriate monoclonal antibodies. After incubation, 1 ml of assay buffer was added to each tube to wash the cells, and the cells were pelleted by centrifugation. The supernatant was removed, and the cells were resuspended in 300-500 ml of assay buffer.

Fresh UBC samples were red blood cell depleted using hetastarch and ammonium chloride lysis or hetastarch and ficoll. 20 ml of cord blood was diluted with an equal volume of PBS and 8 mls of hetastarch (Heta Sep; Stem Cell Technologies, Inc.). Samples were mixed and incubated for 60 minutes at room temperature. The white blood cell fraction was removed from each tube and pelleted by centrifugation. Recovered cells were resuspended in 30 ml of ammonium chloride and incubated at 37° C. for 15-30 minutes or passed over a ficoll gradient to remove contaminating red blood cells. Cells were washed, diluted, and phenotyped with monoclonal antibodies and ALDEFLUOR™ as described above.

Fresh mobilized peripheral blood samples from normal donors and also from cancer patients (i.e., post G-CSF infusion) were diluted 1:20 in ammonium chloride and incubated for 15-30 minutes at 37° C. See, Fields et al. (1994) Cancer Control 1:213 and Elfenbein et al. (1995) *Annal. NY Acad. Sci.* 770:315 for patient procedures. The recovered cells were then washed, diluted, and phenotyped with monoclonal antibodies and ALDEFLUOR™ as described above.

All human samples were obtained using technical and informed consent procedures that complied with relevant regulations and were approved by local institutional review boards.

Multiparameter phenotyping data was acquired on a Becton Dickinson FACSCalibur using an argon laser emission at 488 nm to excite the ALDEFLUOR™ reaction product (fluorescence detected in FL1 channel), phycoerythrin-conjugated antibodies to a large panel of markers (see Table 1; fluorescence detected in FL2 channel); 7-aminoactinomycin D was used to stain and discriminate dead cells (fluorescence detected in FL3 channel), and a HeNe laser was used to excite allophycocyanine-conjugated CD34 (fluorescence detected in FL4). Fluorescence was carefully compensated in multiparameter analysis to correct for spillover of signals among channels (see Table 1 for compensation controls). The ALDH$^{br}$SSC$^{lo}$ cell population was defined by gating on forward and side scatter and FL1. A large data file was acquired such that >2000 events were contained in the ALDH$^{br}$SSC$^{lo}$ gate.

Table 1 shows the percentage of the cells within the ALDH$^{br}$SSC$^{lo}$ window that express the given marker and also the percentage of the total cells in the sample that express the marker that fall outside the ALDH$^{br}$ window. Thus, CD7, primarily a T cell marker, and CD45, a pan-blood cell marker, fall primarily outside the window, while the percentage of stem cell markers such as CD34 and CD133 are increased within the window relative to ungated cells. Notably, not all of the cells expressing stem cell markers are in the window. Therefore, ALDH defines subsets of these stem cell markers, and the populations are different in the three sources. The distribution of the markers in the ALDH$^{br}$ window varies both among tissues and among samples of a given tissue (especially for cord blood), which suggests that the ALDH marker gives more information about the physiological and functional state of the stem cells.

Table 2 shows the percentage of CD34$^+$ cells that also express each of the other markers shown in each tissue. In this table, all markers were analyzed with regard to CD34 and ALDH expression.

Table 3 shows the overall expression of the markers in the three tissues.

Table 4A-C summarizes the expression of CD markers in different gates for bone marrow, umbilical cord blood, and peripheral blood, respectively. The overall expression in the tissue, the expression in the ALDH$^{br}$ gate, and the expression in the CD34$^+$ gate are shown.

Within this gate (ALDH$^{br}$SSC$^{lo}$), it was observed that BM includes more cells capable of giving rise to non-hematopoietic tissues (e.g., positive for CD34, CD105, CD117, and CD133) than populations derived from MPB or UCB based on the phenotypic profile. Moreover, CD105 is expressed to a greater extent in the bone marrow ALDH$^{br}$ cell population than in other grafts. The CD105$^+$ and CD133$^+$ cells are very bright for ALDH in the bone marrow, even brighter than CD34 positive cells. It is possible that CD133$^+$ cells are CD105 positive, but that not all CD105$^+$ cells are CD133 positive. Also, the SSC$^{lo}$ window does not capture all of the CD105/CD133 ALDH cells in marrow, although it does capture the CD34$^+$ cells, which is different in UCB and PBSC. The scatterplots and comparative data supporting these conclusions are shown in FIGS. 1-6.

TABLE 1

Percentage of Cells Expressing CD Marker Shown
Mean and Standard Deviation Summary

| | Bone Marrow (n = 10) | | | | Cord Blood (n = 7) | | | | Peripheral Blood (n = 16) | | | |
|---|---|---|---|---|---|---|---|---|---|---|---|---|
| | % of ALDH$^{br}$ cells expressing marker | | % of cells expressing marker that are NOT ALDH$^{br}$ | | % of ALDHbr cells expressing marker | | % of cells expressing marker that are NOT ALDH$^{br}$ | | % of ALDHbr cells expressing marker | | % of cells expressing marker that are NOT ALDH$^{br}$ | |
| CD Marker | Mean | S.D. | Mean | S.D. | Mean | S.D. | Mean | S.D. | Mean | S.D. | Mean | S.D. |
| CD3 | 1.36 | 0.788 | 99.91 | 0.098 | 1.95 | 1.249 | 99.96 | 0.043 | 1.47 | 1.426 | 99.91 | 0.115 |
| CD7 | 1.31 | 0.798 | 99.78 | 0.384 | 7.36 | 14.051 | 99.92 | 0.083 | 1.02 | 0.845 | 99.84 | 0.236 |
| CD10 | 1.29 | 1.234 | 98.35 | 4.383 | 0.46 | 0.410 | 98.39 | 2.425 | 0.47 | 0.721 | 94.22 | 14.119 |
| CD13 | 7.96 | 8.649 | 99.59 | 0.401 | 16.33 | 21.495 | 99.21 | 1.537 | 24.84 | 26.139 | 98.67 | 2.962 |
| CD14 | 1.68 | 1.755 | 99.78 | 0.202 | 1.13 | 1.359 | 99.97 | 0.021 | 0.66 | 0.798 | 99.96 | 0.051 |
| CD19 | 1.53 | 1.697 | 99.07 | 1.934 | 0.55 | 0.660 | 99.76 | 0.555 | 0.60 | 0.762 | 98.53 | 3.092 |
| CD33 | 7.55 | 7.510 | 98.57 | 3.470 | 12.33 | 13.595 | 99.39 | 1.091 | 18.71 | 22.23 | 99.22 | 1.134 |
| CD34 | 68.96 | 14.630 | 54.19 | 12.978 | 81.41 | 5.252 | 25.60 | 11.454 | 94.85 | 4.405 | 24.39 | 25.683 |

TABLE 1-continued

Percentage of Cells Expressing CD Marker Shown
Mean and Standard Deviation Summary

| | Bone Marrow (n = 10) | | | | Cord Blood (n = 7) | | | | Peripheral Blood (n = 16) | | | |
|---|---|---|---|---|---|---|---|---|---|---|---|---|
| | % of ALDH$^{br\ cells}$ expressing marker | | % of cells expressing marker that are NOT ALDH$^{br}$ | | % of ALDHbr cells expressing marker | | % of cells expressing marker that are NOT ALDH$^{br}$ | | % of ALDHbr cells expressing marker | | % of cells expressing marker that are NOT ALDH$^{br}$ | |
| CD Marker | Mean | S.D. | Mean | S.D. | Mean | S.D. | Mean | S.D. | Mean | S.D. | Mean | S.D. |
| CD35 | 1.57 | 1.239 | 99.43 | 1.500 | 1.01 | 0.974 | 99.95 | 0.053 | 2.37 | 2.65 | 99.73 | 0.667 |
| CD38 | 68.75 | 16.872 | 96.09 | 1.754 | 49.20 | 21.900 | 99.31 | 0.793 | 69.17 | 26.779 | 97.76 | 2.452 |
| CD41-C | 27.22 | 18.522 | 98.95 | 0.695 | 16.89 | 19.567 | 99.43 | 0.521 | 27.26 | 23.166 | 98.52 | 2.910 |
| CD45-M | 54.62 | 18.533 | 99.26 | 0.395 | 78.28 | 20.454 | 99.16 | 0.726 | 86.08 | 21.323 | 98.56 | 2.128 |
| CD56-BD | 2.16 | 1.398 | 97.39 | 2.762 | 4.64 | 9.899 | 99.40 | 0.936 | 1.62 | 2.269 | 98.55 | 3.868 |
| CD90 | 3.22 | 3.532 | 93.87 | 6.810 | 8.00 | 14.188 | 98.88 | 0.984 | 2.52 | 2.356 | 89.10 | 15.818 |
| CD105 | 10.28 | 11.173 | 75.18 | 22.390 | 0.82 | 0.686 | 94.87 | 10.439 | 1.03 | 1.188 | 93.06 | 16.374 |
| CD117 | 43.78 | 23.037 | 72.54 | 14.873 | 45.96 | 26.423 | 43.51 | 8.297 | 18.99 | 18.045 | 45.61 | 17.208 |
| CD127 | 0.74 | 0.688 | 76.77 | 19.260 | 0.39 | 0.255 | 88.66 | 14.759 | 0.54 | 0.657 | 73.89 | 27.193 |
| CD133 | 4.06 | 4.626 | 61.29 | 32.003 | 29.61 | 21.858 | 37.21 | 14.145 | 36.80 | 26.149 | 26.23 | 16.888 |
| CD135 | 0.84 | 0.704 | 84.93 | 18.976 | 1.09 | 1.428 | 90.93 | 15.926 | 0.58 | 0.717 | 81.56 | 19.431 |
| CD138* | 0.71 | 0.740 | 88.36 | 17.536 | 0.11 | | 99.67 | | 0.57 | 0.582 | 76.98 | 24.293 |
| HLA-DR | 38.43 | 16.437 | 97.46 | 1.620 | 65.79 | 20.136 | 98.02 | 1.952 | 64.89 | 26.688 | 95.61 | 4.872 |
| GLY-A | 5.67 | 4.942 | 98.02 | 1.942 | 1.46 | 0.479 | 98.47 | 1.994 | 0.69 | 0.694 | 96.06 | 6.321 |
| ALDH | 0.97 | 0.598 | | | 0.80 | 0.556 | | | 1.11 | 1.084 | | |

*For Bone Marrow CD138: n = 7
*For Cord Blood CD138: n = 1
*For Peripheral Blood CD138: n = 10

TABLE 2

Percentage of CD34+ Cells Expressing CD Marker Shown

| | Bone Marrow (n = 10) | | Cord Blood (n = 7) | | Peripheral Blood (n = 16) | |
|---|---|---|---|---|---|---|
| CD Marker | Mean | STDEV | Mean | STDEV | Mean | STDEV |
| CD3 | 0.69 | 0.348 | 3.15 | 1.863 | 1.86 | 2.371 |
| CD7 | 0.78 | 0.444 | 6.30 | 6.090 | 1.29 | 0.976 |
| CD10 | 8.49 | 8.179 | 1.07 | 1.334 | 0.61 | 0.737 |
| CD13 | 6.09 | 7.420 | 14.60 | 21.476 | 25.16 | 25.962 |
| CD14 | 0.26 | 0.317 | 0.25 | 0.188 | 0.57 | 0.556 |
| CD19 | 3.17 | 3.328 | 1.53 | 0.872 | 0.67 | 0.837 |
| CD33 | 6.52 | 4.710 | 9.70 | 12.607 | 18.25 | 22.459 |
| ALDH | 47.19 | 11.882 | 74.40 | 11.454 | 83.41 | 11.946 |
| CD35 | 0.48 | 0.424 | 1.22 | 1.078 | 2.06 | 2.040 |
| CD38 | 69.92 | 20.245 | 47.80 | 22.845 | 67.65 | 27.161 |
| CD41-C | 25.35 | 19.138 | 16.51 | 21.023 | 26.94 | 23.251 |
| CD45-M | 51.03 | 22.604 | 75.61 | 25.070 | 84.27 | 23.342 |
| CD56-BD | 0.79 | 0.658 | 3.17 | 7.043 | 1.51 | 2.186 |
| CD90 | 1.75 | 3.218 | 6.14 | 11.781 | 1.75 | 1.868 |
| CD105 | 1.34 | 1.256 | 0.23 | 0.187 | 0.78 | 1.128 |
| CD117 | 32.91 | 14.833 | 45.36 | 25.923 | 17.93 | 18.403 |
| CD127 | 0.27 | 0.181 | 0.14 | 0.159 | 0.40 | 0.489 |
| CD133 | 2.78 | 4.016 | 30.74 | 24.161 | 35.63 | 26.734 |
| CD135 | 0.16 | 0.094 | 0.34 | 0.401 | 0.43 | 0.632 |
| CD138 | 0.13 | 0.151 | 0.09 | n/a | 0.43 | 0.584 |
| HLA-DR | 49.76 | 18.578 | 64.26 | 22.024 | 62.44 | 26.427 |
| GLY-A | 0.38 | 0.228 | 0.85 | 0.556 | 0.51 | 0.611 |
| ALDH | 0.97 | 0.599 | 0.80 | 0.556 | 1.11 | 1.085 |
| R3 iso | 0.45 | 0.304 | 0.47 | 0.146 | 0.30 | 0.325 |
| R5 iso | 0.19 | 0.288 | 0.78 | 0.780 | 0.19 | 0.261 |
| R2 pe iso | 3.59 | 8.143 | 0.93 | 0.510 | 0.79 | 0.815 |
| G7 pe iso | 13.51 | 21.887 | 3.37 | 3.064 | 4.57 | 6.799 |

TABLE 3

Percentage of Ungated Cells Expressing Shown Markers

| CD Marker | Bone Marrow (n = 10) Mean | STDEV | Cord Blood (n = 6) Mean | STDEV | Peripheral Blood Mean | STDEV |
|---|---|---|---|---|---|---|
| | | | | | (n = 16) | |
| CD3 | 14.72 | 3.727 | 43.69 | 14.643 | 21.81 | 18.080 |
| CD7 | 8.38 | 2.719 | 43.76 | 17.460 | 14.85 | 15.860 |
| CD10 | 3.73 | 2.290 | 0.79 | 0.847 | 0.72 | 0.933 |
| CD13 | 19.42 | 8.313 | 22.12 | 10.275 | 45.08 | 27.214 |
| CD14 | 5.24 | 1.362 | 22.62 | 3.440 | 25.43 | 11.399 |
| CD19 | 2.68 | 1.751 | 6.45 | 3.990 | 4.69 | 8.967 |
| CD33 | 15.51 | 9.257 | 23.73 | 3.985 | 25.98 | 17.523 |
| CD34 | 1.40 | 0.500 | 0.90 | 0.517 | 0.98 | 1.082 |
| CD35 | 9.58 | 8.285 | 20.08 | 8.910 | 41.67 | 21.568 |
| CD38 | 17.66 | 3.871 | 71.88 | 18.735 | 36.31 | 18.805 |
| CD41-C | 26.32 | 14.980 | 22.33 | 5.725 | 41.81 | 19.781 |
| CD45-M | 70.51 | 13.339 | 88.84 | 12.651 | 96.93 | 4.692 |
| CD56-BD | 1.07 | 0.854 | 5.90 | 7.961 | 3.98 | 4.527 |
| CD90 | 1.88 | 3.681 | 6.24 | 10.195 | 0.72 | 0.347 |
| CD105 | 0.53 | 0.367 | 1.44 | 2.131 | 2.36 | 4.736 |
| CD117 | 1.52 | 0.582 | 0.67 | 0.500 | 0.24 | 0.308 |
| CD127 | 0.07 | 0.053 | 0.59 | 1.012 | 1.03 | 2.686 |
| CD133 | 0.12 | 0.113 | 0.32 | 0.255 | 0.27 | 0.151 |
| CD135 | 0.15 | 0.119 | 0.34 | 0.463 | 0.10 | 0.080 |
| CD138 | 0.07 | 0.060 | 0.37 | #DIV/0! | 0.04 | 0.012 |
| HLA-DR | 14.92 | 2.690 | 31.27 | 6.338 | 21.49 | 10.799 |
| GLY-A | 9.16 | 5.722 | 3.07 | 2.110 | 0.47 | 0.379 |
| ALDH | 0.97 | 0.599 | 0.80 | 0.556 | 1.11 | 1.085 |
| | | | | | n = 9 | |
| R3 iso | 0.45 | 0.304 | 0.47 | 0.146 | 0.30 | 0.325 |
| R5 iso | 0.19 | 0.288 | 0.78 | 0.780 | 0.19 | 0.261 |
| R2 pe iso | 3.59 | 8.143 | 0.93 | 0.510 | 0.79 | 0.815 |
| G7 pe iso | 13.51 | 21.887 | 3.37 | 3.064 | 4.57 | 6.799 |
| CD45 APC | 79.57 | 11.861 | 89.39 | 10.992 | 96.96 | 2.178 |
| AB45 APC | 71.45 | 25.804 | 66.33 | 24.573 | 79.89 | 21.902 |

TABLE 4A

Summary of Bone Marrow (All Gates)

| | Bone Marrow | | | | | |
|---|---|---|---|---|---|---|
| | ALDH CD+ | | CD34CD+ | | CD+ | |
| CD Marker | Mean % | St. Dev. | Mean % | St. Dev. | Mean % | St. Dev. |
| CD3 | 1.36 | 0.788 | 0.69 | 0.348 | 14.72 | 3.727 |
| CD7 | 1.31 | 0.798 | 0.78 | 0.444 | 8.38 | 2.719 |
| CD10 | 1.29 | 1.234 | 8.49 | 8.179 | 3.73 | 2.290 |
| CD13 | 7.96 | 8.649 | 6.09 | 7.420 | 19.42 | 8.313 |
| CD14 | 1.68 | 1.755 | 0.26 | 0.317 | 5.24 | 1.362 |
| CD19 | 1.53 | 1.697 | 3.17 | 3.328 | 2.68 | 1.751 |
| CD33 | 7.55 | 7.510 | 6.52 | 4.710 | 15.51 | 9.257 |
| ALDH | 68.96 | 14.630 | 47.19 | 11.882 | 1.40 | 0.500 |
| CD35 | 1.57 | 1.239 | 0.48 | 0.424 | 9.58 | 8.285 |
| CD38 | 68.75 | 16.872 | 69.92 | 20.245 | 17.66 | 3.871 |
| CD41-C | 27.22 | 18.522 | 25.35 | 19.138 | 26.32 | 14.980 |
| CD45-M | 54.62 | 18.533 | 51.03 | 22.604 | 70.51 | 13.339 |
| CD56-BD | 2.16 | 1.398 | 0.79 | 0.658 | 1.07 | 0.854 |
| CD90 | 3.22 | 3.532 | 1.75 | 3.218 | 1.88 | 3.681 |
| CD105 | 10.28 | 11.173 | 1.34 | 1.256 | 0.53 | 0.367 |
| CD117 | 43.78 | 23.037 | 32.91 | 14.833 | 1.52 | 0.582 |
| CD127 | 0.74 | 0.688 | 0.27 | 0.181 | 0.07 | 0.053 |
| CD133 | 4.06 | 4.626 | 2.78 | 4.016 | 0.12 | 0.113 |
| CD135 | 0.84 | 0.704 | 0.16 | 0.094 | 0.15 | 0.119 |
| CD138 | 0.71 | 0.740 | 0.13 | 0.151 | 0.07 | 0.060 |
| HLA-DR | 38.43 | 16.437 | 49.76 | 18.578 | 14.92 | 2.690 |
| GLY-A | 5.67 | 4.942 | 0.38 | 0.228 | 9.16 | 5.722 |

TABLE 4B

Summary of Cord Blood (All Gates)

| | Cord Blood | | | | | |
|---|---|---|---|---|---|---|
| | ALDH CD+ | | CD34CD+ | | CD+ | |
| CD Marker | Mean | STDEV | Mean | STDEV | Mean | STDEV |
| CD3 | 1.95 | 1.249 | 3.15 | 1.863 | 43.69 | 14.643 |
| CD7 | 7.36 | 14.051 | 6.30 | 6.090 | 43.76 | 17.460 |
| CD10 | 0.46 | 0.410 | 1.07 | 1.334 | 0.79 | 0.847 |
| CD13 | 16.33 | 21.495 | 14.60 | 21.476 | 22.12 | 10.275 |
| CD14 | 1.13 | 1.359 | 0.25 | 0.188 | 22.62 | 3.440 |
| CD19 | 0.55 | 0.660 | 1.53 | 0.872 | 6.45 | 3.990 |
| CD33 | 12.33 | 13.595 | 9.70 | 12.607 | 23.73 | 3.985 |
| ALDH | 81.41 | 5.252 | 74.40 | 11.454 | 0.90 | 0.517 |
| CD35 | 1.01 | 0.974 | 1.22 | 1.078 | 20.08 | 8.910 |
| CD38 | 49.20 | 21.900 | 47.80 | 22.845 | 71.88 | 18.735 |
| CD41-C | 16.89 | 19.567 | 16.51 | 21.023 | 22.33 | 5.725 |
| CD45-M | 78.28 | 20.454 | 75.61 | 25.070 | 88.84 | 12.651 |
| CD56-BD | 4.64 | 9.899 | 3.17 | 7.043 | 5.90 | 7.961 |
| CD90 | 8.00 | 14.188 | 6.14 | 11.781 | 6.24 | 10.195 |
| CD105 | 0.82 | 0.686 | 0.23 | 0.187 | 1.44 | 2.131 |
| CD117 | 45.96 | 26.423 | 45.36 | 25.923 | 0.67 | 0.500 |
| CD127 | 0.39 | 0.255 | 0.14 | 0.159 | 0.59 | 1.012 |
| CD133 | 29.61 | 21.858 | 30.74 | 24.161 | 0.32 | 0.255 |
| CD135 | 1.09 | 1.428 | 0.34 | 0.401 | 0.34 | 0.463 |
| CD138 | 0.11 | | 0.09 | | 0.37 | |
| HLA-DR | 65.79 | 20.136 | 64.26 | 22.024 | 31.27 | 6.338 |
| GLY-A | 1.46 | 0.479 | 0.85 | 0.556 | 3.07 | 2.110 |

TABLE 4C

Summary of Peripheral Blood (All Gates)

| | Peripheral Blood | | | | | |
|---|---|---|---|---|---|---|
| | ALDH CD+ | | CD34CD+ | | CD+ | |
| CD Marker | Mean | STDEV | Mean | STDEV | Mean | STDEV |
| CD3 | 1.47 | 1.426 | 1.86 | 2.371 | 21.81 | 18.080 |
| CD7 | 1.02 | 0.845 | 1.29 | 0.976 | 14.85 | 15.860 |
| CD10 | 0.47 | 0.721 | 0.61 | 0.737 | 0.72 | 0.933 |
| CD13 | 24.84 | 26.139 | 25.16 | 25.962 | 45.08 | 27.214 |
| CD14 | 0.66 | 0.798 | 0.57 | 0.556 | 25.43 | 11.399 |
| CD19 | 0.60 | 0.762 | 0.67 | 0.837 | 4.69 | 8.967 |
| CD33 | 18.71 | 22.23 | 18.25 | 22.459 | 25.98 | 17.523 |
| ALDH | 94.85 | 4.405 | 83.41 | 11.946 | 0.98 | 1.082 |
| CD35 | 2.37 | 2.65 | 2.06 | 2.040 | 41.67 | 21.568 |
| CD38 | 69.17 | 26.779 | 67.65 | 27.161 | 36.31 | 18.805 |
| CD41-C | 27.26 | 23.166 | 26.94 | 23.251 | 41.81 | 19.781 |
| CD45-M | 86.08 | 21.323 | 84.27 | 23.342 | 96.93 | 4.692 |
| CD56-BD | 1.62 | 2.269 | 1.51 | 2.186 | 3.98 | 4.527 |
| CD90 | 2.52 | 2.356 | 1.75 | 1.868 | 0.72 | 0.347 |
| CD105 | 1.03 | 1.188 | 0.78 | 1.128 | 2.36 | 4.736 |
| CD117 | 18.99 | 18.045 | 17.93 | 18.403 | 0.24 | 0.308 |
| CD127 | 0.54 | 0.657 | 0.40 | 0.489 | 1.03 | 2.686 |
| CD133 | 36.80 | 26.149 | 35.63 | 26.734 | 0.27 | 0.151 |
| CD135 | 0.58 | 0.717 | 0.43 | 0.632 | 0.10 | 0.080 |
| CD138 | 0.57 | 0.582 | 0.43 | 0.584 | 0.04 | 0.012 |
| HLA-DR | 64.89 | 26.688 | 62.44 | 26.427 | 21.49 | 10.799 |
| GLY-A | 0.69 | 0.694 | 0.51 | 0.611 | 0.47 | 0.379 |
| ALDH | 1.11 | 1.084 | 1.11 | 1.085 | 1.11 | 1.085 |

Example 2

Visualization and Characterization of the ALDH$^{br}$ SSC$^{lo}$ Cells having the Phenotype of Interest For intracellular staining, FACS™ isolated ALDH$^{br}$SSC$^{lo}$ cells having the phenotype of interest, as identified in Example 1, are stained using the Fix and Penn cell permeabilization kit according to the manufacturer's instructions (Caltag Laboratories). In preparation for differential Wright Giemsa staining, cells in PBS are pelleted for 3 minutes at 1000 rpm directly onto coated slides using a Cytospin3 centrifuge. The cells are stained with Wright Giemsa stain in an automated cell stainer.

Example 3

Functional Characterization of ALDH$^{br}$SSC$^{lo}$, Cells having the Phenotype of Interest Using In Vitro Culture Hematopoietic progenitor colony HPC assays are performed by plating 100-200 ALDH$^{br}$SSC$^{lo}$ cells having the phenotype of interest, as identified in Example 1, in MethoCult H4431 (StemCell Technologies, Inc.). The cells are incubated in a humidified chamber at 37° C. with 5% CO$_2$. Hematopoietic colonies (>100 cells) are then scored at 14-18 days after initiating the cultures. See, for example, Fallon et al (2003) Br. J. Haematol. 121:1, herein incorporated by reference in its entirety.

Long-term culture (LTC) assays are performed by maintaining ALDH$^{br}$SSC$^{lo}$ cells having the phenotype of interest, as identified in Example 1, on either irradiated allogeneic bone marrow stroma or stromal layers of murine MS-5 cells (Issaad et al. (1993) Blood 81:2916) or in some instances S17 cells (with medium containing Flt3 ligand, IL-3, erythropoietin, G-CSF, and IL-15) according to the method of Fallon et al. (2003) Br. J. Haematol. 121:1. MS-5 cells support the growth of human multipotent cells and BFU-E for extended periods of time and may support early stem cells as well as, or better than, standard allogeneic stroma. The stromal layers are established by seeding the center wells of 24-well plates (Corning Costar Corp.) with 6-7×10$^4$ MS-5 cells/well in 0.5 ml DMEM supplemented with 10% FCS. These cells are cultured at 37° C. in a humidified incubator until the cultures approach approximately 80% confluence. The monolayers are then irradiated with 30 Gy γ-irradiation from a cesium source. After irradiation, the culture media from the monolayers is replaced entirely with Myelocult H5100 (StemCell Technologies, Inc.) and the cells are maintained at 33° C. in a humidified chamber with 5% CO$_2$. Long-term cultures are typically initiated with 500-20,000 sorted hematopoietic progenitor cells/well on the irradiated MS-5 cells. At 7-10 day intervals, half the media from each well is removed so that the media can be replenished. Adherent and non-adherent cells are harvested after 2 weeks and plated into HPC assays as described above. The HPC assay generally identifies relatively mature progenitor cells with limited lineage and self-renewal potential, while the LTC assay generally quantifies more primitive cells with a higher self-renewal potential.

Example 4

Large Segmental Canine Femoral Defects are Healed with Autologous Stem Cell Therapy The stem cells of the invention are used in a canine model of bone engraftment. See, for example, U.S. Pat. No. 6,541,024 herein incorporated by reference in its entirety. The following protocols are used for culture-expanding autologous mesenchymal stem cells of the invention that can regenerate clinically significant bone defects in a large animal model.

MSC Cultivation and Manipulation

A 15 cc bone marrow aspirate is obtained from the iliac crest of each animal, according to an IACUC-approved protocol, and shipped on ice by overnight courier to the cell culture facilities. Isolation of canine ALDH$^{br}$ MSCs is achieved using procedures described in Example 1. Tissue culture flasks (185 cm$^2$) are seeded with 10$^7$ nucleated cells isolated from the cushion, and cultured with DMEM containing 10% fetal calf serum from a selected lot. Cells are passaged at 8×10$^3$ cells/cm$^2$, and maintained until the time of implantation. Cell-loaded implants are prepared by incubating fibronectin-coated porous hydroxyapatite-tricalcium phosphate (HA/TCP) cylinders (Zimmer, Inc.) in a 7.5×10$^6$ cells/ml suspension of MSCs for 3 hr at 37° C. The interval between marrow harvest and implantation is 16 days. An aliquot of cells from each preparation is also cultured under osteoinductive conditions to quantify aspects of osteoblastic differentiation.

Canine Femoral Gap Model

A unilateral segmental femoral defect model is developed for this study following IACUC approval. Under general anesthesia, thirty-six skeletally mature female purpose-bred hounds (20 kg) undergo resection of a 21 mm long osteoperiosteal segment from their mid-diaphysis. A 4.5 mm Synthes™ 8-hole lengthening plate is contoured to the lateral aspect of the bone, and secured with bicortical screws. The defect is filled with one of three materials; 1) a cell-free HA/TCP cylinder, 2) an MSC-loaded HA/TCP cylinder, or 3) cancellous bone harvested from the iliac crest. HA/TCP implants are secured by placing two sutures around the implant and the plate. Animals receive peri-operative antibiotics, and analgesics are administered for three days post-operatively.

Radiographic and Histologic Analyses

Standard radiographic images are obtained at pre-op, immediately post-op, and at 4 week intervals until termination of the study. All samples contain a radiodensity step wedge to provide a basis for comparing changes over time, and between dogs. Upon sacrifice, specimens are subjected to high resolution Faxitron radiography, and subsequently processed for biomechanical evaluation. Following torsion testing, undecalcified longitudinal sections will be processed for quantitative histomorphometry.

Biomechanical Testing

Sixteen weeks after implantation, animals are sacrificed for torsion testing of femurs. The fixation plate, screws, and adherent soft tissue are removed, and the metaphyses of the bones are embedded. The specimens are externally rotated in a custom torsion test apparatus, failure load and stiffness recorded, and the data analyzed by one way ANOVA according to post hoc Student-Newman-Keuls tests.

Results

Generally, animals tolerate the surgical procedure well, with no incidence of infection, implant rejection, or failure of fixation. Two modes of repair are generally observable in the MSC-loaded samples; first, considerable callus formation generally occurs at both host-implant interfaces; and second, a substantial collar of bone surrounding the implant itself develops. Cell-free implants generally do not possess either of these features. Autograft samples generally undergo a traditional consolidation sequence, with the majority of bone being laid down in the medial aspect of the gap defect. Generally, MSC-loaded samples not only became fully integrated at the host implant interface, but the periosteal collar extended proximally and distally beyond the cut edges of the gap. Furthermore, the diameter of new bone at the mid-diaphysis is generally greater in MSC-loaded implants than either autograft samples or intact limbs. Analyses of the osteogenic potential MSCs from each animal generally demonstrate the development of alkaline phosphatase-positive cells which deposit significant mineralized extracellular matrix.

Example 5

Myocardial Infarcts are Healed with Autologous Stem Cell Therapy

The stem cells of the invention are used in a porcine model of myocardial infarction. See for example, Dib et al (2002) *J. Endovasc. Ther.* 9:313. The following protocols are used for culture-expanding autologous mesenchymal stem cells of the invention that can regenerate clinically significant heart damage in a large animal model.

Animal Preparation 7-month-old swine undergo baseline cardiovascular evaluation and serve as the recipient animal for myoblast transplantation. A 12-lead electrocardiogram (ECG) is obtained, and 2-dimensional transthoracic echocardiography is performed to assess wall motion and ejection fraction. An 8-F arterial sheath is inserted into the right femoral artery using a cutdown technique, and selective left and right coronary angiography and left ventriculography are performed using the right anterior oblique and left anterior oblique projections.

Three-dimensional (3D) electromechanical mapping is performed using the NOGA Biosense Navigational System via a 7-F NOGA B-curve catheter advanced through the 8-F sheath into the left ventricle. The electromechanical activity of the myocardium is determined based on the maps constructed from 35 acquired points.

Concurrent with the femoral cutdown, a 6-cm incision is made longitudinally along the right hind leg. Under sterile conditions, a 5-g segment of the thigh muscle is removed. The muscle segment is placed in a cell transportation medium on ice and sent to a cell culturing facility for myoblast expansion.

Infarction Model

An anterior infarct is induced in the host swine via coil embolization using individual 3- and 4-mm Vortx™ coils delivered to the middle left anterior descending artery. Coronary occlusion occurs 2 minutes after coil placement, as demonstrated by coronary angiography. A postinfraction left ventriculogram, echo cardiogram, and ECG are performed within 5 minutes of infarction. Significant ventricular arrhythmias are treated with a 2% intravenous lidocaine bolus and electrical cardioversion. The femoral artery is sutured, the incision is closed, and the animal was is per standard operating procedures Myoblast Isolation The skeletal muscle myoblasts are isolated through a series of steps described in Example 1. The cells are plated in a growth medium composed of Dulbecco's Modified Eagle Medium with 10% (vol/vol) fetal bovine serum and 0.5% (vol/vol) gentamicin. The cells are maintained at <70% density and allowed to expand over a 4-week period, replacing one half of the growth medium with fresh medium every other day. Cells are visually examined daily and growth curves are obtained.

In preparation for cell injection, the myoblasts are harvested using 0.05% trypsin/ethylenediaminetetraacetic acid; trypsin is inactivated by the addition of growth medium containing fetal bovine serum. The cells are centrifuged and washed twice. The resulting cell pellet is resuspended in 2.5 mL of serum-free Dulbecco's Modified Eagle Medium.

Allogenic Myoblast Transplantation

Four weeks after creating the infarction, the animals are anesthetized with intramuscular Telozol (tiletamine hydrochloride and zolazepam hydrochloride; 500 mg), intubated, and mechanically ventilated with 2% isoflurane and 3-L/min oxygen. An 8-F arterial sheath is inserted into the left femoral artery using a cutdown technique and cardiovascular assessments are repeated (ECG, echocardiography, left ventriculography, and coronary angiography). Electromechanical mapping identifies the infracted area.

Using a B-curve needle injection catheter calibrated to extend 4 to 5 mm into the endocardium, approximately 200 million cells in the 2.5-mL suspension are injected into 25 arbitrarily selected sites (0.1 mL each) at the center and periphery of the infracted myocardium. Penetration of the endocardium is verified by ST elevations and premature ventricular contractions during needle advancement. The injection sites are delineated on the electromechanical map. After the injections are completed, the sheath is removed, the femoral artery is sutured, and the animal is allowed to recover.

Ten days later, the animals are anesthetized and euthanized. The heart is harvested, rinsed in saline, and preserved in 10% formalin prior to section in 5-mm increments from apex to base. Thin sections (8 μm) from the infarct region are stained either with hematoxylin and eosin (H&E) or Masson's trichrome.

Generally after the above procedures, cardiac function is restored to pre-infarction levels. This includes functional measures both for overall cardiac function via ECG and histological function as measured by pathology performed on tissues after animal sacrifice.

Example 6

Characterization of Bone Marrow Derived Cells in Culture

Bone marrow (Sample #40411) was processed as in Example 1. Phenotype was determined on the starting population. The $ALDH^{br}SSC^{lo}$ population was sorted, and 1.8× $10^5$ cells were cultured in Cambrex MSCGM™-Mesenchymal Stem Cell Medium (Product #3238). Non-adherent cells were removed after 7 days, and adherent cells were expanded following manufacturer's instructions for 4 weeks when the phenotype panel was repeated. Results show the percentage of cells expressing ALDH and other markers before and after the culture period (Table 5). These data illustrate that adherent cells with the phenotype of mesenchymal stem cells grew out.

TABLE 5

| Marker(s) | % Cells Expressing marker at time shown | |
|---|---|---|
|  | Start | Week 4 |
| $ALDH^{br}SSC^{lo}$ | 0.6 | 10.9 |
| CD34 | 0.9 | 0.3 |
| CD133 | 0.2 | 0.2 |
| $CD34^+CD133^+$ | 13.9 | 0.0 |
| CD73 |  | 96.7 |
| CD105 | 0.6 | 95.2 |
| CD166 |  | 72.8 |
| VEGF-R2 |  | 0.5 |
| CD45 |  | 0.9 |
| CD31 |  | 0.9 |
| $ALDH^{br}SSC^{lo}/CD34^+$ | 80.9 | 0.0 |
| $ALDH^{br}SSC^{lo}/CD133^+$ | 21.6 | 0.0 |
| $ALDH^{br}SSC^{lo}/CD73^+$ |  | 97.3 |
| $ALDH^{br}SSC^{lo}/CD105^+$ | 23.7 | 95.7 |

TABLE 5-continued

| Marker(s) | % Cells Expressing marker at time shown | |
|---|---|---|
| | Start | Week 4 |
| $ALDH^{br}SSC^{lo}/CD166^+$ | | 66.4 |
| $ALDH^{br}SSC^{lo}/VEGF-R2^+$ | | 0.2 |
| $ALDH^{br}SSC^{lo}/CD45^-$ | | 99.5 |
| $ALDH^{br}SSC^{lo}/CD31^+$ | | 0.3 |
| $ALDH^{br}SSC^{lo}/CD14^+$ | | 0.4 |
| CD14 | | 1.4 |

Example 7

Characterization and Culture of Bone Marrow Derived Cells from Multiple Donors

Hematopoietic progenitor colony assays were performed for $ALDH^{br}SSC^{lo}$ cells sorted from normal human bone marrow. Bone marrow samples with phenotypes shown on Table 6 were sorted to prepare $ALDH^{br}SSC^{lo}$ populations.

TABLE 6

| Marker(s) | % of cells with marker phenotype shown in marrow from donor # shown | | | | |
|---|---|---|---|---|---|
| | 30411 | 30418 | 30426 | 40404 | Average |
| $ALDH^{br}SSC^{lo}$ | 0.6 | 1.4 | 1.5 | 1.2 | 1.2 |
| CD34 | 0.9 | 1.1 | 1.8 | 0.9 | 1.2 |
| CD133 | 0.2 | 0.1 | 0.0 | 0.0 | 0.1 |
| $CD34^+CD133^+$ | 13.9 | 1.5 | 1.2 | 0.0 | 4.1 |
| CD73 | | | 3.3 | 1.1 | 2.2 |
| CD105 | 0.6 | 1.0 | 1.4 | 0.2 | 0.8 |
| CD166 | | | 0.7 | 0.1 | 0.4 |
| VEGF-R2 | | 0.4 | 8.8 | 0.2 | 3.1 |
| CD45 | | | 95.2 | 92.8 | 94.0 |
| CD31 | | | 78.4 | 70.8 | 74.6 |
| $ALDH^{br}SSC^{lo}/CD34^+$ | 80.9 | 37.1 | 30.7 | 27.3 | 44.0 |
| $ALDH^{br}SSC^{lo}/CD133^+$ | 21.6 | 7.2 | 1.0 | 0.2 | 7.5 |
| $ALDH^{br}SSC^{lo}/CD73^+$ | | | 0.9 | 0.4 | 0.7 |
| $ALDH^{br}SSC^{lo}/CD105^+$ | 23.7 | 46.9 | 52.8 | 5.2 | 32.1 |
| $ALDH^{br}SSC^{lo}/CD166^+$ | | | 5.8 | 0.3 | 3.0 |
| $ALDH^{br}SSC^{lo}/VEGF-R2^+$ | | 11.5 | 9.3 | 0.6 | 7.2 |
| $ALDH^{br}SSC^{lo}/CD45^-$ | | | 36.7 | 50.1 | 43.4 |
| $ALDH^{br}SSC^{lo}/CD31^+$ | | | 38.6 | 33.2 | 35.9 |

Figure 7:
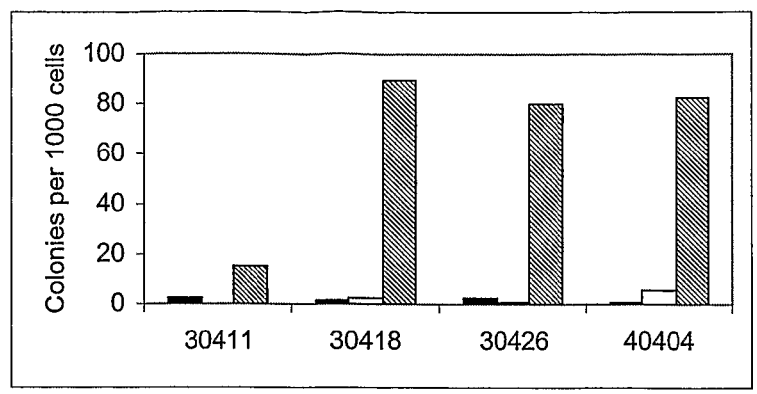
FIG. 7 shows the results of hematopoietic progenitor colony forming assays for four bone marrow samples cultured for two weeks. Filled bars are data for marrow samples following removal of erythrocytes; open bars are cell suspensions following reaction with the ALDH substrate but prior to sorting; and hatched bars are enriched ALDH$^{br}$SSC$^{lo}$ populations after staining.

Cells were cultured for two weeks in standard methylcellulose colony forming assays. All cultures formed multilineage colonies (FIG. 7). Data shown in FIG. 7 are total colony counts per 1000 cells input. Filled bars are data for marrow samples following removal of erythrocytes with ammonium chloride treatment; open bars are cell suspensions following reaction with the ALDH substrate but prior to sorting; and hatched bars are enriched $ALDH^{br}SSC^{lo}$ populations after staining. These data illustrate that markers typical of earlier endothelial progenitors such as CD31 and VEGF receptor are present and, in most cases, enriched in the $ALDH^{br}$ population.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

That which is claimed:

1. A cell population of $ALDH^{br}$ stem cells, wherein at least 10% of the cells within said population express at least CD105, and wherein said population is capable of multilineage development.

2. The cell population of claim 1, wherein said stem cells are derived from bone marrow.

3. The cell population of claim 1, wherein at least 10% of the cells within said population also express at least one cell surface marker selected from the group consisting of CD34, CD38, CD41, CD45, CD117, CD133, HLA-DR, and combinations thereof, wherein said population is substantially free of cells expressing cell surface markers selected from the group consisting of CD3, CD7, CD10, CD13, CD14, CD19, CD33, CD35, CD56, CD127, CD138, glycophorin A, and combinations thereof, and wherein said population of cells is capable of multilineage development.

4. The cell population of claim 1, wherein greater than about 60% of the cells within the population express the cell surface marker CD105.

5. The cell population of claim 1, wherein at least 10% of the cells within the population are side scatter channel low ($SSC^{lo}$).

6. The cell population of claim 1, wherein said population is capable of engrafting a mammal.

7. The cell population of claim 6, wherein said population is capable of engrafting hematopoietic cells.

8. The cell population of claim 6, wherein said population is capable of engrafting a SCID/NOD mouse spleen with human B cell precursors.

9. The cell population of claim 6, wherein said population is capable of engrafting human thymus tissue transplanted into SCID/hu Thy mice with T cell precursors.

10. The cell population of claim 9, wherein said T cell precursors are capable of developing into T cells expressing CD4 or CD8.

11. The cell population of claim 6, wherein said population is capable of engrafting mesenchymal cells.

12. The cell population of claim 11, wherein said population is capable of engrafting tissue selected from the group consisting of bone marrow stroma, bone, cartilage, tendon, fat, smooth muscle, cardiac muscle, skeletal muscle, nerves, oligodendrocytes, fibroblasts, endothelium, and combinations thereof.

13. A composition comprising the cell population of claim 1 in a pharmacologically acceptable carrier.

14. A cell population of bone-marrow-derived, ALDH$^{br}$ stem cells, wherein said cells are capable of multilineage development.

15. The cell population of claim 14, wherein at least 10% of the cells within said population express a cell surface marker selected from the group consisting of CD34, CD38, CD41, CD45, CD105, CD117, CD133, HLA-DR, and combinations thereof, wherein said population is substantially free of cells expressing cell surface markers selected from the group consisting of CD3, CD7, CD10, CD13, CD14, CD19, CD33, CD35, CD56, CD127, CD138, glycophorin A, and combinations thereof, and wherein said population of cells is capable of multilineage development.

16. The cell population of claim 15, wherein at least 10% of the cells within said population express at least CD105.

17. The cell population of claim 16, wherein at least 40% of the cells within said population express at least CD105.

18. The cell population of claim 14, wherein at least 10% of the cells within the population are side scatter channel low (SSC$^{lo}$).

19. The cell population of claim 14, wherein said population is capable of engrafting a mammal.

20. The cell population of claim 19, wherein said population is capable of engrafting hematopoietic cells.

21. The cell population of claim 19, wherein said population is capable of engrafting a SCID/NOD mouse spleen with human B cell precursors.

22. The cell population of claim 19, wherein said population is capable of engrafting human thymus tissue transplanted into SCID/hu Thy mice with T cell precursors.

23. The cell population of claim 22, wherein said T cell precursors are capable of developing into T cells expressing CD4 or CD8.

24. The cell population of claim 19, wherein said population is capable of engrafting mesenchymal cells.

25. The cell population of claim 24, wherein said population is capable of engrafting tissue selected from the group consisting of bone marrow stroma, bone, cartilage, tendon, fat, smooth muscle, cardiac muscle, skeletal muscle, nerves, oligodendrocytes, fibroblasts, endothelium, and combinations thereof.

26. A composition comprising the cell population of claim 14 in a pharmacologically acceptable carrier.

* * * * *